United States Patent
Rapoport et al.

(10) Patent No.: US 8,350,012 B2
(45) Date of Patent: Jan. 8, 2013

(54) INVERSE AGONIST MONOCLONAL ANTIBODY THAT SUPPRESSES THYROTROPIN RECEPTOR CONSTITUTIVE ACTIVITY

(75) Inventors: Basil Rapoport, Santa Monica, CA (US); Sandra McLachlan, Santa Monica, CA (US); Chun-Rong Chen, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 611 days.

(21) Appl. No.: 12/519,513

(22) PCT Filed: Jan. 24, 2008

(86) PCT No.: PCT/US2008/051866
§ 371 (c)(1),
(2), (4) Date: Jun. 16, 2009

(87) PCT Pub. No.: WO2008/091981
PCT Pub. Date: Jul. 31, 2008

(65) Prior Publication Data
US 2011/0014200 A1    Jan. 20, 2011

Related U.S. Application Data

(60) Provisional application No. 60/886,564, filed on Jan. 25, 2007.

(51) Int. Cl.
*C07K 16/28* (2006.01)
*C07K 16/00* (2006.01)

(52) U.S. Cl. ............ 530/388.22; 530/388.1; 530/387.9; 530/387.3; 435/810

(58) Field of Classification Search .................. None
See application file for complete search history.

(56) References Cited

U.S. PATENT DOCUMENTS 6,228,597 B1 * 5/2001 Parmentier et al. ............ 435/7.1
2003/0138836 A1    7/2003 Evans et al.

FOREIGN PATENT DOCUMENTS

WO    2006002774 A1    1/2006

OTHER PUBLICATIONS

Chen et al. (Endocrinology, Jul. 2009, 150(7):3401-3408.*
Owens et al. (JIM, 1994, 168:149-165).*
Lederman et al. (Molecular Immunology 28: 1171-1181, 1991).*
Li et al. (PNAS 77: 3211-3214, 1980).*
Houghten et al. (New Approaches to Immunization, Vaccines 86, Cold Spring Harbor Laboratory, p. 21-25, 1986).*
Ando et al. Thyrotropin receptor anitbodies: new insights into their actions and clinical relevance. Best Practice & Research. (2005). 19(1): 33-52.
PCT/US2008/051866 IPRP dated Jul. 28, 2009.
PCT/US2008/051866 Written Opinion dated Aug. 13, 2008.

* cited by examiner

*Primary Examiner* — Sharon Wen
(74) *Attorney, Agent, or Firm* — Linda B. Huber; Nixon Peabody LLP

(57) ABSTRACT

This invention describes monoclonal antibodies that suppress thyrotropin receptor constitutive activity and methods of using the antibodies to treat thyroid related diseases; particularly hyperthyroidism and thyroid cancer.

23 Claims, 11 Drawing Sheets

Fig. 7

MRPADLLQLVLLLDLPRDLGGMGCSSPPCECHQEEDFRVTCKDIQRIPSLPPSTQTLKLIETHLRTIPSHAFS
NLPNISRIYVSIDVTLQQLESHSFYNLSKVTHIEIRNTRNLTYIDPDALKELPLLKFLGIFNTGLKMFPDLTKVYS
TDIFFILEITDNPYMTSIPVNAFQGLCNETLTLKLYNNGFTSVQGYAFNGTKLDAVYLNKNKYLTVIDKDAFGG
VYSGPSLLDVSQTSVTALPSKGLEHLKELIARNTWTLKKLPLSLSFLHLTRADLSYPSHCCAFKNQKKIRGILE
SLMCNESSMQSLRQRKSVNALNSPLHQEYEENLGDSIVGYKEKSKFQDTHNNAHYVFFEEQEDEIIGFGQ
ELKNPQEETLQAFDSHYDYTICGDSEDMVCTPKSDEFNPCEDIMGYKFLRIVWFVSLLALLGNVFVLLILLT
SHYKLNVPRFLMCNLAFADFCMGMYLLIASVDLYTHSEYYNHAIDWQTGPGCNTAGFFTVFASELSVYTLT
VITLERVVYAITFAMRLDRKIRLRHACAIMVGGWVCCFLLALLPLVGISSYAKVSICLPMDTETPLALAYIVFVLT
LNIVAFVIVCCCHVKIYITVRNPQYNPGDKDTKIAKRMAVLIFTDFICMAPISFYALSAILNKPLITVSNSKILLVLF
YPLNSCANPFLYAIFTKAFQRDVFILLSKFGICKRQAQAYRGQRVPPKNSTDIQVQKVTHDMRQGLHNMED
VYELIENSHLTPKKQGQISEEYMQTVL

Fig. 8

AFQGLCNETLTLKLYNNGFTSVQGYAFNGTKLDAVYLNKNKYLTVIDKDAFGGVYSGPSLLDVSQTSVTA
LPSKGLEHLKELIARNTWTL

Fig. 9

```
ATGAGGGCGGCGGACTTGCTGCAGCTGGTCTGCTGCTGACCTGCTGCTGCCCAGGACCTGGGCGGAATGGGGTGTTCGTCT
CCACCCTGCGAGTGCCATCAGGAGGAGGACTTCAGATGCAACTGCCCAAGGATATTCAACGCATCCCCAGCTTCAACGCCCA
GTACGCAGACTCTGAAGCTCTTATTGAGACTCGAGAGCTGGAACTGCACCTTCCAAGTCATCATTTCTGCCCAATATTCCAG
AATCTACGTATCTATAGATGTGACTCTGCAGCAGCTGGAATCACACTCCTTCTACAATTGAGTAAAGTGACTCACATAGA
AATTCGGAATACCAGGAACTTAACTTACATAGACCCTGATGCCCTCAAAGAGCTCCCCTCCTAAAGTTCCTTGGCATTT
CAACACTGGACTTAAAATGTTCCCTGACCAAAGTTTATTCCACTGATATATTCTTTATACTTGAAATTACAGACAAC
CCTTACATGACGTCAATCCCTGTGAATGCTTTCAGGGACTATGCAATGAAACCTTGACACTGAAGCTGTACAACAATGGC
TTACTTCAGTCCAAGGATATGCTTTCAATGGGACAAAGCTGGACTTGCTGTTTACCTAAACAAGAATAAATACCTGACAGTTA
TTGACAAAGATGCATTTGGAGGAGTATACAGTGGACCAAGCTTGCTGACGTGTCTCAAACCAGTGTCACTTTCCTTGAGTTTC
TCCAAAGGCCTGGAGCACCTGACCTGCTGCTTTAAGAATCAGAAGAGAAATCAGAGGAATCCTT
CTTCACCTCACACGGGCTGTAATGAGAGCAGTATGCAGAGCTTGCGCAGAGAAATCTGTGAATGCCTTGAATAGCCCCCTCCA
GAGTCCCTTGATGTGTATGAAGAGAATCTGGGTGACAGCATTGTTGGGTACAAGTCCAAGTTCCAGGATACTCATAACAACG
CCAGGAATATGAAGAGAATCTGGGTGACAGCATTGTTGGGTACAAGTCCAAGTTCCAGGATACTCATAACAACG
CTCATTATTACGTCTCTTGAAGAACCATTATGACTACACACCATATGTGGGGACAGTGAAGACATGGTGTACCCCAAGTCCGAT
CTCTACAAGCTTTGACAGCCATTATGACTACACACCATATGTGGGGACAGTGAAGACATGGTGTACCCCAAGTCCGAT
GAGTTCAACCGTGTCTTTGTCCTGCTTATTCTCCTCACCAGCAGCTGTACAAGTTCCTGAGAATTGTGGTGTCGTTAGTCTGCTCTCCT
GGGCAATGTCTTTGTCCTGCTTATTCTCCTCACCAGCAGCTGTACAAGTTCCTGAGAATTGTGGTGTCGTTAGTCTGCTCTCCT
CTTTGCGGATTCTGCAGCTGGACAGACCCTGGGTGCAACACGGCTGGTTTCTTCACTGTCTCTTGCAAGCGGAAGATCCGCCTCAGGCA
TGCCATCGACTGGCAGCCCTGGAGCGCTGGTATGCCATGACCTTCGCCATGCCCTGCCATGCCCCTGCTCTTCCTTGGTGGGAATAAGTAGCTATG
CGCTGACGGTGCCATCATGGTTGGGGGCTGTGGGTTTGCTGCTTCCGCCATGCCCCTGCTCTTCCTTGGTGGGAATAAGTAGCTATG
CCAAAGTCAGTATCTGCTCGTCGTCGTCCCCATGGACACCGAGACCCCTTTGCTGCTCCGCCAAATCCGCAGTACAACCCAGGGGAC
TAGTTGCCTTGCCTTCGTCATCGTCTGCTCGTCGTCGTCGTCCCCATGGACACCGAGACCCCTTTGCTGCTCCGCCAAATCCGCAGTACAACCCAGGGGAC
AAAGATACCAAAATTGCCAAGAGATGGCTCTCATCAGAGGATGGCTCTCATCTTTCACCGACTTCATCTTTGCTGGTACTCTCTATCCACTTAACTCCT
CTGTCAGCAATTCTGAACAAGTCCTTCTATTTCACCAAGGCCTTCACCAAGGGATGTGTTCATCCTACTCAGCAAGTTTGGCATCT
GTGCCAATCCATTCCTCTATGCTCATACCGGGGACATACCGGGGCAGAGGGTTCCTCCAAGAACAGCACTGATATTCAGGTTCAAAGGTTAC
GTAAACGCCAGGTCAGGACTCAGGCATACCGGGGCAGAGGGTTCCTCCAAGAACAGCACTGATATTCAGGTTCAAAGGTTAC
CCACGACGACATGAGGCAGGGTCTCCACAACATGGAAGATGTCTATGAACTGATTGAAACTCCATGAACTCCAAGCTAA
AAGGCCAAATCTCAGAAGAGTATATGCAAACGGTTTTGTAA
```

Fig. 10

GCTTTTCAGGGACTATGCAATGAAACCTTGACACTGAAGCTGTACAACAATGGCTTACTTCAGTCCAAGGATATG
CTTTCAATGGGACAAAGCTGGATGCTGTGTTTACCTAAACAAGAATAAATACCTGACAGTTATTGACAAAGATGCATT
GGAGGAGTATACCAGTGGACCAAGCTTGCTGGACGTGTCTCAAACCAGTGTCACTGCCCTTCCATCCAAAGGCCTG
GAGCACCTGAAGGAACTGATAGC

SEQUENCE LISTING

<160> NUMBER OF SEQ ID NOS: 4

<210> SEQ ID NO 1
<211> LENGTH: 764
<212> TYPE: PRT
<213> ORGANISM: Homo sapiens

<400> SEQUENCE: 1

```
Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
    130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
    210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
    290                 295                 300

Ser Met Gln Ser Leu Arg Gln Arg Lys Ser Val Asn Ala Leu Asn Ser
305                 310                 315                 320

Pro Leu His Gln Glu Tyr Glu Glu Asn Leu Gly Asp Ser Ile Val Gly
                325                 330                 335

Tyr Lys Glu Lys Ser Lys Phe Gln Asp Thr His Asn Asn Ala His Tyr
            340                 345                 350

Tyr Val Phe Phe Glu Glu Gln Glu Asp Glu Ile Ile Gly Phe Gly Gln
        355                 360                 365
```

Glu Leu Lys Asn Pro Gln Glu Thr Leu Gln Ala Phe Asp Ser His
    370                 375                 380

Tyr Asp Tyr Thr Ile Cys Gly Asp Ser Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Ala Leu Leu Gly Asn
            420                 425                 430

Val Phe Val Leu Leu Ile Leu Leu Thr Ser His Tyr Lys Leu Asn Val
        435                 440                 445

Pro Arg Phe Leu Met Cys Asn Leu Ala Phe Ala Asp Phe Cys Met Gly
    450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
        515                 520                 525

Leu Asp Arg Lys Ile Arg Leu Arg His Ala Cys Ala Ile Met Val Gly
    530                 535                 540

Gly Trp Val Cys Cys Phe Leu Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Val Phe Val Leu Thr Leu Asn Ile Val
            580                 585                 590

Ala Phe Val Ile Val Cys Cys Cys His Val Lys Ile Tyr Ile Thr Val
        595                 600                 605

Arg Asn Pro Gln Tyr Asn Pro Gly Asp Lys Asp Thr Lys Ile Ala Lys
    610                 615                 620

Arg Met Ala Val Leu Ile Phe Thr Asp Phe Ile Cys Met Ala Pro Ile
625                 630                 635                 640

Ser Phe Tyr Ala Leu Ser Ala Ile Leu Asn Lys Pro Leu Ile Thr Val
                645                 650                 655

Ser Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
        675                 680                 685

Val Phe Ile Leu Leu Ser Lys Phe Gly Ile Cys Lys Arg Gln Ala Gln
    690                 695                 700

Ala Tyr Arg Gly Gln Arg Val Pro Pro Lys Asn Ser Thr Asp Ile Gln
705                 710                 715                 720

Val Gln Lys Val Thr His Asp Met Arg Gln Gly Leu His Asn Met Glu
                725                 730                 735

Asp Val Tyr Glu Leu Ile Glu Asn Ser His Leu Thr Pro Lys Lys Gln
            740                 745                 750

Gly Gln Ile Ser Glu Glu Tyr Met Gln Thr Val Leu
        755                 760

<210> SEQ ID NO 2
<211> LENGTH: 90
<212> TYPE: PRT

<213> ORGANISM: Homo sapiens

<400> SEQUENCE: 2

```
Ala Phe Gln Gly Leu Cys Asn Glu Thr Leu Thr Leu Lys Leu Tyr Asn
1               5                   10                  15

Asn Gly Phe Thr Ser Val Gln Gly Tyr Ala Phe Asn Gly Thr Lys Leu
            20                  25                  30

Asp Ala Val Tyr Leu Asn Lys Asn Lys Tyr Leu Thr Val Ile Asp Lys
        35                  40                  45

Asp Ala Phe Gly Gly Val Tyr Ser Gly Pro Ser Leu Leu Asp Val Ser
    50                  55                  60

Gln Thr Ser Val Thr Ala Leu Pro Ser Lys Gly Leu Glu His Leu Lys
65                  70                  75                  80

Glu Leu Ile Ala Arg Asn Thr Trp Thr Leu
                85                  90
```

<210> SEQ ID NO 3
<211> LENGTH: 2295
<212> TYPE: DNA
<213> ORGANISM: Homo sapiens

<400> SEQUENCE: 3

| | | | | | |
|---|---|---|---|---|---|
| atgaggccgg | cggacttgct | gcagctggtg | ctgctgctcg | acctgcccag | ggacctgggc | 60 |
| ggaatggggt | gttcgtctcc | accctgcgag | tgccatcagg | aggaggactt | cagagtcacc | 120 |
| tgcaaggata | ttcaacgcat | ccccagctta | ccgcccagta | cgcagactct | gaagcttatt | 180 |
| gagactcacc | tgagaactat | tccaagtcat | gcattttcta | atctgcccaa | tatttccaga | 240 |
| atctacgtat | ctatagatgt | gactctgcag | cagctggaat | cacactcctt | ctacaatttg | 300 |
| agtaaagtga | ctcacataga | aattcggaat | accaggaact | taacttacat | agaccctgat | 360 |
| gccctcaaag | agctcccccct | cctaaagttc | cttggcattt | tcaacactgg | acttaaaatg | 420 |
| ttccctgacc | tgaccaaagt | ttattccact | gatatattcc | ttatacttga | aattacagac | 480 |
| aaccccttaca | tgacgtcaat | ccctgtgaat | gcttttcagg | gactatgcaa | tgaaaccttg | 540 |
| acactgaagc | tgtacaacaa | tggctttact | tcagtccaag | gatatgcttt | caatgggaca | 600 |
| aagctggatg | ctgtttacct | aaacaagaat | aaatacctga | cagttattga | caaagatgca | 660 |
| tttggaggag | tatacagtgg | accaagcttg | ctggacgtgt | ctcaaaccag | tgtcactgcc | 720 |
| cttccatcca | aaggcctgga | gcacctgaag | gaactgatag | caagaaacac | ctggactctt | 780 |
| aagaaacttc | cactttcctt | gagtttcctt | cacctcacac | gggctgacct | ttcttaccca | 840 |
| agccactgct | gtgcttttaa | gaatcagaag | aaaatcagag | gaatccttga | gtccttgatg | 900 |
| tgtaatgaga | gcagtatgca | gagcttgcgc | cagagaaaat | ctgtgaatgc | cttgaatagc | 960 |
| cccctccacc | aggaatatga | agagaatctg | ggtgacagca | ttgttgggta | caaggaaaag | 1020 |
| tccaagttcc | aggatactca | taacaacgct | cattattacg | tcttctttga | agaacaagag | 1080 |
| gatgagatca | ttggttttgg | ccaggagctc | aaaaaccccc | aggaagagac | tctacaagct | 1140 |
| tttgacagcc | attatgacta | caccatatgt | ggggacagtg | aagacatggt | gtgtaccccc | 1200 |
| aagtccgatg | agttcaaccc | gtgtgaagac | ataatgggct | acaagttcct | gagaattgtg | 1260 |
| gtgtggttcg | ttagtctgct | ggctctcctg | gcaatgtct | ttgtcctgct | tattctcctc | 1320 |
| accagccact | acaaactgaa | cgtcccccgc | tttctcatgt | gcaacctggc | cttgcggat | 1380 |
| ttctgcatgg | ggatgtacct | gctcctcatc | gcctctgtag | acctctacac | tcactctgag | 1440 |
| tactacaacc | atgccatcga | ctggcagaca | ggccctgggt | gcaacacggc | tggtttcttc | 1500 |

```
actgtctttg caagcgagtt atcggtgtat acgctgacgg tcatcaccct ggagcgctgg    1560
tatgccatca ccttcgccat gcgcctggac cggaagatcc gcctcaggca cgcatgtgcc    1620
atcatggttg ggggctgggt ttgctgcttc cttctcgccc tgcttccttt ggtgggaata    1680
agtagctatg ccaaagtcag tatctgcctg cccatggaca ccgagacccc tcttgctctg    1740
gcatatattg ttttgttct gacgctcaac atagttgcct tcgtcatcgt ctgctgctgt    1800
tatgtgaaga tctacatcac agtccgaaat ccgcagtaca acccagggga caaagatacc    1860
aaaattgcca agaggatggc tgtgttgatc ttcaccgact tcatatgcat ggccccaatc    1920
tcattctatg ctctgtcagc aattctgaac aagcctctca tcactgttag caactccaaa    1980
atcttgctgg tactcttcta tccacttaac tcctgtgcca atccattcct ctatgctatt    2040
ttcaccaagg ccttccagag ggatgtgttc atcctactca gcaagtttgg catctgtaaa    2100
cgccaggctc aggcataccg ggggcagagg gttcctccaa agaacagcac tgatattcag    2160
gttcaaaagg ttacccacga catgaggcag ggtctccaca acatggaaga tgtctatgaa    2220
ctgattgaaa actcccatct aaccccaaag aagcaaggcc aaatctcaga agagtatatg    2280
caaacggttt tgtaa                                                     2295

<210> SEQ ID NO 4
<211> LENGTH: 251
<212> TYPE: DNA
<213> ORGANISM: Homo sapiens

<400> SEQUENCE: 4
gcttttcagg gactatgcaa tgaaaccttg acactgaagc tgtacaacaa tggctttact      60
tcagtccaag gatatgcttt caatgggaca aagctggatg ctgtttacct aaacaagaat     120
aaatacctga cagttattga caaagatgca tttggaggag tatacagtgg accaagcttg     180
ctggacgtgt ctcaaaccag tgtcactgcc cttccatcca aaggcctgga gcacctgaag     240
gaactgatag c                                                          251
```

INVERSE AGONIST MONOCLONAL ANTIBODY THAT SUPPRESSES THYROTROPIN RECEPTOR CONSTITUTIVE ACTIVITY

CROSS-REFERENCE TO RELATED APPLICATIONS

This application is the National Phase of International Application No. PCT/US08/51866, filed Jan. 24, 2008, which designated the U.S. and that International Application was published under PCT Article 21(2) in English. This application also includes a claim of priority under 35 U.S.C. §119(e) to U.S. provisional patent application No. 60/886,564, filed Jan. 25, 2007.

GOVERNMENT RIGHTS

The U.S. Government has a paid-up license in this invention and the right in limited circumstances to require the patent owner to license others on reasonable terms as provided for by the terms of Grant No. RO1DK19289 awarded by the National Institutes of Health.

FIELD OF INVENTION

This invention relates to monoclonal antibodies that suppress thyrotropin receptor constitutive activity and methods of treating thyroid diseases.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The thyrotropin receptor (TSHR), a member of the G protein-coupled receptor (GPCR) superfamily, is a key regulator of thyroid function. Through the TSHR, the natural ligand, thyrotropin (TSH), and pathological autoantibodies (primarily stimulatory but occasionally blocking) modify cAMP generation by adenylyl cyclase and, consequently, many aspects of thyroid hormone synthesis and secretion (Vassart et al. 1992. The thyrotropin receptor and the regulation of thyrocyte function and growth. *Endocr. Rev.* 13:596-611; Rapoport et al. 1998. The thyrotropin receptor: Interaction with thyrotropin and autoantibodies. *Endocr. Rev.* 19:673-716.). TSH also induces thyrocyte growth and proliferation (Vassart et al. 1992. The thyrotropin receptor and the regulation of thyrocyte function and growth. *Endocr. Rev.* 13:596-611.). The TSHR is structurally similar to the receptors for the other anterior pituitary glycoprotein hormones (Vassart et al. 2004. A molecular dissection of the glycoprotein hormone receptors. *Trends Biochem. Sci.* 29:119-126), yet is functionally different in possessing relatively high constitutive activity in the absence of ligand (Van Sande et al. 1995. In Chinese hamster ovary K1 cells dog and human thyrotropin receptors activate both the cyclic AMP and the phosphatidylinositol 4,5-bisphosphate cascades in the presence of thyrotropin and the cyclic AMP cascade in its absence. *Eur. J. Biochem.* 229:338-343). This activity is partially constrained by the TSHR ectodomain (Zhang et al. 2000. The extracellular domain suppresses constitutive activity of the transmembrane domain of the human TSH receptor: implications for hormone-receptor interaction and antagonist design. *Endocrinol.* 141:3514-3517) that, therefore, functions as an inverse agonist (Vlaeminck-Guillem et al. 2002. Activation of the cAMP pathway by the TSH receptor involves switching of the ectodomain from a tethered inverse agonist to an agonist. *Mol. Endocrinol.* 16:736-746). Significant TSHR constitutive activity is a clinically relevant phenomenon in the treatment of thyroid carcinoma. After thyroidectomy, suppression of endogenous TSH secretion is a therapeutic goal to prevent or retard the proliferation or metastasis of residual thyroid carcinoma cells. However, even complete TSH suppression with supra-physiological doses of thyroxine cannot eliminate potentially harmful TSHR activity. Also, perhaps because of its inherent 'noisiness', the TSHR is highly susceptible to activation by a large variety of disease-inducing mutations, particularly within its serpentine region, as documented in a recent data base (Van Durme et al. 2006. GRIS: glycoprotein-hormone receptor information system. *Mol. Endocrinol.* 20:2247-2255).

In recent years, understanding of TSHR structure and function has been greatly facilitated by the generation of murine (Loosfelt et al. 1992. Two-subunit structure of the human thyrotropin receptor. *Proc. Natl. Acad. Sci. U.S.A.* 89:3765-3769; Huang et al. 1993. The thyrotropin hormone receptor of Graves' disease: overexpression of the extracellular domain in insect cells using recombinant baculovirus, immunoaffinity purification and analysis of autoantibody binding. *J. Mol. Endocrinol.* 10:127-142; Johnstone et al. 1994. Monoclonal antibodies that recognize the native human thyrotropin receptor. *Molec. Cell. Endocrinol.* 105:R1-R9; Seetharamaiah et al. 1995. Generation and characterization of monoclonal antibodies to the human thyrotropin (TSH) receptor: antibodies can bind to discrete conformational or linear epitopes and block TSH binding. *Endocrinol.* 136:2817-2824; Costagliola et al. 1998. Genetic immunization against the human thyrotropin receptor causes thyroiditis and allows production of monoclonal antibodies recognizing the native receptor. *J. Immunol.* 160:1458-1465; Oda et al. 2000. Epitope analysis of the human thyrotropin (TSH) receptor using monoclonal antibodies. *Thyroid* 10:1051-1059; Sanders et al. 2002. Thyroid stimulating monoclonal antibodies. *Thyroid* 12:1043-1050; Costagliola et al. 2002. Generation of a mouse monoclonal TSH receptor antibody with stimulating activity. *Biochem. Biophys. Res. Commun.* 299:891-896; Gilbert et al. 2006. Monoclonal pathogenic antibodies to the TSH receptor in Graves' disease with potent thyroid stimulating activity but differential blocking activity activate multiple signaling pathways. *J. Immunol.* 176:5084-5092; Costagliola et al. 2004. Delineation of the discontinuous-conformational epitope of a monoclonal antibody displaying full in vitro and in vivo thyrotropin activity. *Mol. Endocrinol.* 18:3020-3024), hamster (Ando et al. 2002. A monoclonal thyroid-stimulating antibody. *J. Clin. Invest* 110:1667-1674) and human (Akamizu et al. 1999. Characterization of recombinant monoclonal anti-thyrotropin receptor antibodies (TSHRAbs) derived from lymphocytes of patients with Graves' disease: epitope and binding study of two stimulatory TSHRAbs. *Endocrinol.* 140:1594-1601; Sanders et al. S. B. 2003. Human monoclonal thyroid stimulating autoantibody. *Lancet* 362:126-128.) monoclonal antibodies (mAb). Of particular interest and importance are those mAb that are potent activators of the TSHR (Sanders et al. 2002. Thyroid stimulating monoclonal antibodies. *Thyroid* 12:1043-1050; Gilbert et al. 2006. Monoclonal pathogenic antibodies to the TSH receptor in Graves' disease with potent thyroid stimulating activity but differential blocking activity activate multiple signaling pathways. *J. Immunol.* 176:5084-5092; Costagliola et al. 2004. Delineation of the discontinuous-conformational epitope of a monoclonal antibody displaying full in vitro and in vivo thyrotropin activity. *Mol Endocrinol.* 18:3020-3024; Ando et al. 2002. A monoclonal thyroid-stimulating antibody. *J. Clin. Invest* 110:1667-1674; Sanders et al. S. B. 2003. Human monoclonal thyroid stimulating autoantibody. *Lancet* 362: 126-128.) Monoclonal antibodies that function as competitive antagonists for thyroid stimulating autoantibodies (TSAb) have also received attention as possible therapeutic agents in Graves' disease (Lenzner et al. 2003. The effect of thyrotropin-receptor blocking antibodies on stimulating autoantibodies from patients with Graves' disease. *Thyroid* 13:1153-1161; Sanders et al. 2005. Characteristics of a monoclonal antibody to the thyrotropin receptor that acts as a powerful thyroid-stimulating autoantibody antagonist. *Thyroid* 15:672-682), although competition for TSH binding, a universal property of these blocking antibodies, will lead to hypothyroidism.

In recent years, the realization that many GPCR have ligand-independent constitutive activity to varying degrees has introduced a new classification of pharmacological agents. Besides agonists and antagonists, inverse agonists and neutral antagonists are now described. Inverse agonists reduce ligand-independent constitutive activity. Many classical competitive antagonists also have inverse agonist properties, unlike neutral antagonists (Bond et al. 2006. Recent developments in constitutive receptor activity and inverse agonism, and their potential for GPCR drug discovery. *Trends Pharmacol. Sci.* 27:92-96.). The search for inverse agonists as therapeutic agents to modulate GPCR expression is of much current interest (Ellis, C. 2004. The state of GPCR research in 2004. *Nat. Rev. Drug Discov.* 3:575, 577-575, 626.). The great majority of GPCR inverse agonists are small molecules, many used in clinical practice as drugs to reduce activity of receptors such as those for epinephrine, histamine, dopamine and angiotensin. In general, these agents bind to a pocket within the transmembrane helices. However, in a few cases, large antibody molecules have been generated that function as inverse agonists by binding to the extracellular loops of the β2-adrenergic (Peter et al. 2003. scFv single chain antibody variable fragment as inverse agonist of the beta2-adrenergic receptor. *J. Biol. Chem.* 278:36740-36747) and M2-muscarinic acetylcholine (Peter et al. 2004. Modulation of the M2 muscarinic acetylcholine receptor activity with monoclonal anti-M2 receptor antibody fragments. *J. Biol. Chem.* 279:55697-55706.) receptors.

Turning to the thyroid, the thyrotropin releasing hormone (TRH) receptors in the pituitary thyrotroph (Straub et al. 1990. Expression cloning of a cDNA encoding the mouse pituitary thyrotropin-releasing hormone receptor. *Proc. Natl. Acad. Sci. U.S.A.* 87:9514-9518; Itadani et at 1998. Cloning and characterization of a new subtype of thyrotropin-releasing hormone receptors. *Biochem. Biophys. Res. Commun.* 250:68-71; Cao et al. 1998. Cloning and characterization of a cDNA encoding a novel subtype of rat thyrotropin-releasing hormone receptor. *J. Biol. Chem.* 273:32281-32287.) and the TSHR in the thyrocyte (Nagayama at al. 1989. Molecular cloning, sequence and functional expression of the cDNA for the human thyrotropin receptor. *Biochem. Biophys. Res. Comm.* 165:1184-1190; Parmentier et al. 1989. Molecular cloning of the thyrotropin receptor. *Science* 246:1620-1622.) are both GPCRs. The former receptor, activated by a small ligand (TRH), has a small extracellular domain. The TSHR has a large ectodomain (397 amino acid residues after signal peptide deletion) consistent with its large (~30 kDa), glycosylated ligand (TSH). Besides their natural ligands, small, synthetic molecules have been sought to modulate receptor function. For example, midozalam has been identified as an inverse agonist for the TRH receptor (Colson et al. 1998. A hydrophobic cluster between transmembrane helices 5 and 6 constrains the thyrotropin-releasing hormone receptor in an inactive conformation. *Mol. Pharmacol.* 54:968-978.) and another synthetic compound (org41821) is a partial agonist for the TSHR (Jaschke et al. 2006. A low molecular weight agonist signals by binding to the transmembrane domain of thyroid-stimulating hormone receptor (TSHR) and luteinizing hormone/chorionic gonadotropin receptor (LHCGR). *J. Biol. Chem.* 281:9841-9844.). Unlike TSH, org41821 interacts directly with TSHR transmembrane helices (Jaschke et al. 2006. A low molecular weight agonist signals by binding to the transmembrane domain of thyroid-stimulating hormone receptor (TSHR) and luteinizing hormone/chorionic gonadotropin receptor (LHCGR). *J. Biol. Chem.* 281:9841-9844.). A modification of this compound acts allosterically as an antagonist of TSH action (Moore et al. 2006. Evaluation of small-molecule modulators of the luteinizing hormone/choriogonadotropin and thyroid stimulating hormone receptors: structure-activity relationships and selective binding patterns. *J. Med. Chem.* 49:3888-3896.). However, no TSHR inverse agonist has been reported.

With the high constitutive activity of TSHR, the risks associated with suppressing TSH, and the side effect of other thyroid cancer and thyroid disease treatments, there exist a need in the art for an inverse agonist of TSHR, and a method to decrease the constitutive activity of TSHR.

SUMMARY OF THE INVENTION

The following embodiments and aspects thereof are described and illustrated in conjunction with compositions and methods which are meant to be exemplary and illustrative, not limiting in scope.

The present invention describes a purified antibody that binds specifically to a thyrotropin receptor ("TSHR") and has inverse agonist activity on the TSHR. In one particular embodiment, the TSHR may be a mutant TSHR. In another particular embodiment, the TSHR may be human TSHR. In another embodiment, the purified antibody may be humanized or may be a human antibody. In one embodiment, the purified antibody may be a monoclonal antibody produced by hybridoma CS-17, ATCC accession number PTA-8174. In another embodiment, the purified antibody may have the same epitope specificity as a monoclonal antibody produced by hybridoma CS-17, ATCC accession number PTA-8174.

In one embodiment, the TSHR may be a polypeptide as disclosed by SEQ ID NO: 1. Alternatively, the TSHR may be a polypeptide at least 95%, 96%, 97%, 98% or 99% identical to SEQ ID NO: 1. In another embodiment, the purified antibody binds specifically to the α-domain of the TSHR.

In another embodiment, the purified antibody binds specifically to a conformational epitope of TSHR, wherein at least a substantial portion of the conformational epitope may be located between amino acid residues 171 and 260 of the TSHR. The amino acid residues 171 through 260 may be as disclosed by SEQ ID NO: 2. Alternatively, the amino acid residues 171 through 260 may be at least 95%, 96%, 97%, 98%, or 99% identical to SEQ ID NO: 2.

The present invention also describes a purified antibody that binds specifically to a polypeptide that is encoded by a polynucleotide that is at least 95%, 96%, 97%, 98% or 99% identical to SEQ ID NO: 3 and has inverse agonist activity on the polypeptide. In particular embodiments, the purified antibody may be humanized or may be a human antibody. In one embodiment, the purified antibody may bind specifically to a conformational epitope on the polypeptide. In another embodiment, a substantial portion of the conformational epitope may be on a polypeptide that is encoded by a polynucleotide that is at least 95%, 96%, 97%, 98% or 99% identical to SEQ ID NO: 4. Alternatively, a substantial portion of the conformational epitope may on a polypeptide encoded by a polynucleotide as disclosed by SEQ ID NO: 4.

In another embodiment, the purified antibody may bind specifically to a polypeptide that is encoded by the polynucleotide as disclosed by SEQ ID NO: 3. In one embodiment, the purified antibody may bind specifically to a conformational epitope on the polypeptide encoded by the polynucleotide as disclosed by SEQ ID NO: 3. A substantial portion of the conformational epitope may be on a polypeptide encoded by a polynucleotide as disclosed by SEQ ID NO: 4.

The present invention also describes a cell of hybridoma CS-17, ATCC accession number PTA-8174.

The present invention also describes a method of treating a thyroid or thyroid-related disease or disease condition in a subject in need thereof, comprising: providing a purified antibody that binds specifically to thyrotropin receptor ("TSHR") and has inverse agonist activity on TSHR as described herein; and administering a therapeutically effective amount of the purified antibody to the subject to treat the thyroid or thyroid-related disease or disease condition.

In various embodiments, the thyroid or thyroid-related disease or disease condition may be selected from the group consisting of thyroid cancer, hyperthyroidism, thyrotoxicosis and combinations thereof. In particular embodiments, the thyroid cancer may be a type selected from the group consisting of papillary, follicular, medullary, anaplastic and combinations thereof.

In an embodiment wherein the thyroid or thyroid-related disease or disease condition is thyroid cancer, administering the purified antibody may comprise administering the purified antibody concurrently with treatment for radio-iodine ablation of residual thyroid cells or administering the purified antibody after surgical removal of thyroid carcinoma and/or radio-iodine ablation of residual thyroid cells.

In various embodiments, the therapeutically effective amount may be about 25 µg to about 250 µg, an amount that will bring a serum level to about 0.01 µg/ml to about 250 µg/ml, or an amount that will bring a serum level to about 100 µg/ml.

The present invention additionally describes a method of suppressing thyrotropin receptor ("TSHR") constitutive activity in a subject in need thereof, comprising: providing a purified antibody that binds specifically to TSHR and has inverse agonist activity on TSHR as described herein; and administering a therapeutically effective amount of the purified antibody to the subject to induce inverse agonist activity on TSHR.

The present invention further describes a kit for the treatment of a thyroid or thyroid-related disease or disease condition in a subject in need thereof, comprising: a purified antibody that binds specifically to thyrotropin receptor ("TSHR") and has inverse agonist activity on TSHR as described herein; and instructions for using the purified antibody to treat the thyroid or thyroid-related disease or disease condition.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 7 depicts an amino acid sequence of human TSHR in accordance with an embodiment of the present invention.

FIG. 8 depicts amino acid residues 171-260 of human TSHR in accordance with an embodiment of the present invention.

FIG. 9 depicts a human TSHR nucleotide coding region in accordance with an embodiment of the present invention.

FIG. 10 depicts a human TSHR nucleotide coding region for amino acid residues within residues 171-260 in accordance with an embodiment of the present invention.

DESCRIPTION OF THE INVENTION

Figure 1:
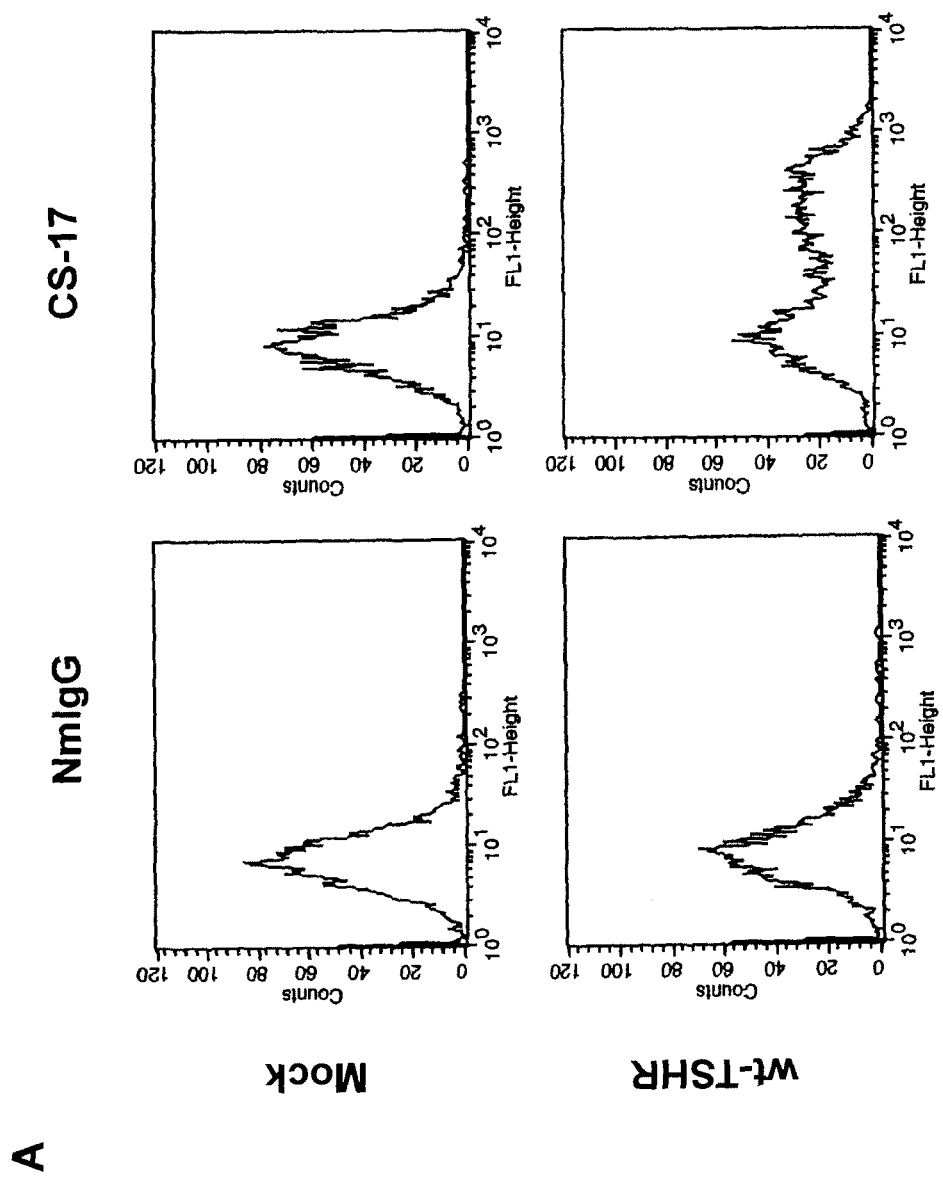
FIG. 1 depicts TSHR mAb CS-17 having inverse agonist activity in accordance with an embodiment of the present invention. Panel A: Flow cytometric recognition by CS-17 (10 µg/ml) of the wild-type TSHR on the cell surface. COS-7 cells were transiently transfected with a plasmid expressing the wild-type (wt) TSHR. As controls, cells were subjected to the transfection procedure without plasmid (mock) and flow cytometry was performed using purified normal mouse IgG (NmIgG) at the same concentration (10 µg/ml). Panel B: Purified CS-17 and control mAb (4C1), both at 10 µg/ml, were incubated for 60 min with aliquots of the same COS-7 cells used for flow cytometry (Panel A). The contribution of the TSHR to intracellular cAMP levels (TSHR transfected vs. mock transfected cells) indicates constitutive TSHR activity. CS-17, but not 4C1, suppressed TSHR constitutive activity (*, p=0.0052; Student's t-test). Data shown are the mean+ range of values from duplicate wells, and are representative of at least 10 experiments. Panel C: Dose-effect relationship of TSHRmAb CS-17 on TSHR constitutive activity. COS-7 cells transiently transfected with the wild-type TSHR were incubated for 60 min with the indicated CS-17 concentrations. Mock transfected cells were included as controls. Intracellular cAMP was measured in duplicate wells of cells. Values indicate the mean±range. Similar data were obtained in a separate experiment.
Figure 1:
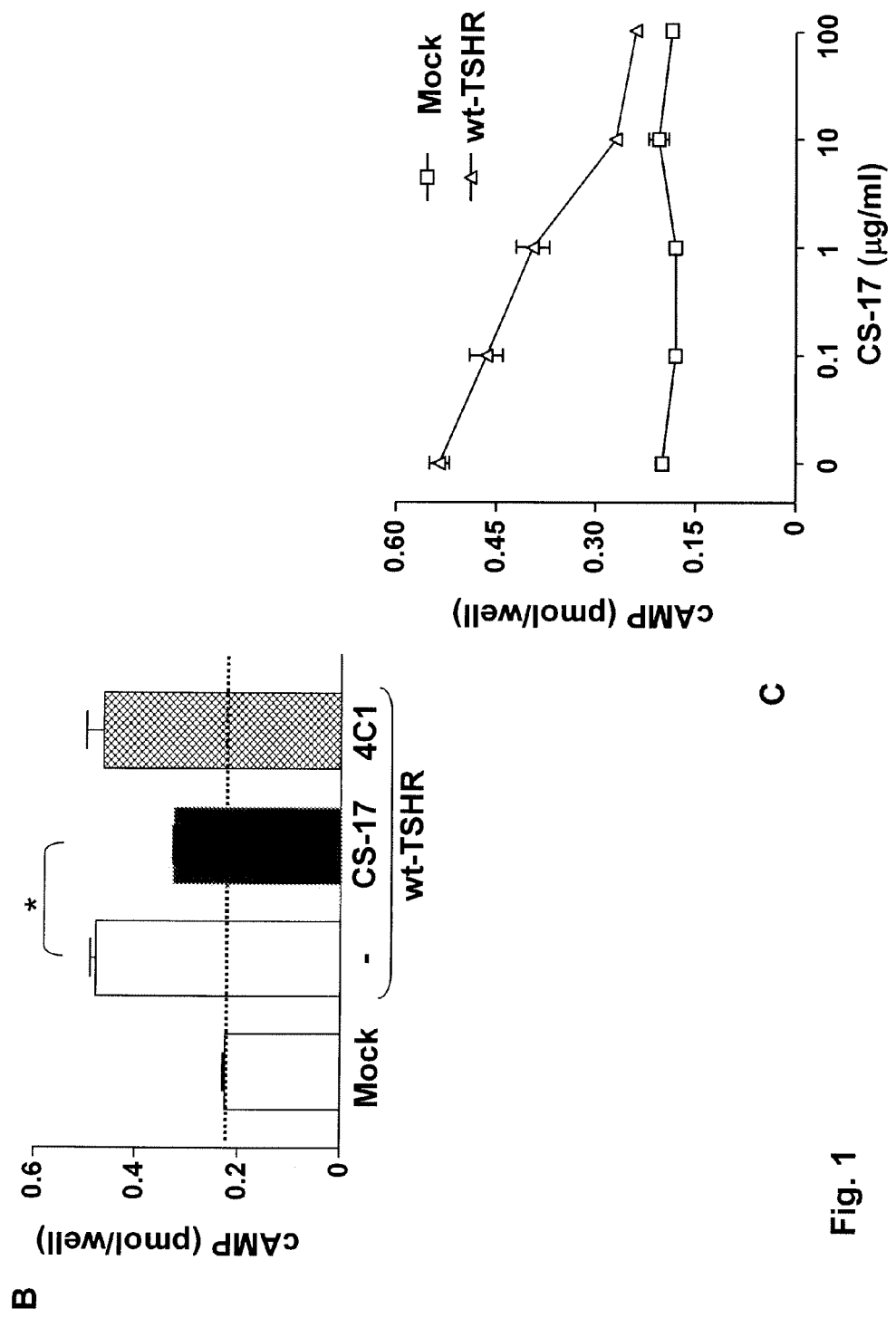

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); Sambrook and Russel, *Molecular Cloning: A Laboratory Manual* 3rd ed., Cold Spring Harbor Laboratory Press (Cold Spring Harbor, N.Y. 2001); D. Lane, *Antibodies: A Laboratory Manual* Cold Spring Harbor Press (Cold Spring Harbor N.Y., 1988); Kohler and Milstein, (1976) Eur. J. Immunol. 6: 511; Queen et al. U.S. Pat. No. 5,585,089; and Riechmann et al., Nature 332: 323 (1988); and G. Subramanian, *Antibodies: Volume* 1: *Production and Purification*, Springer (2005), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Antibody" or "antibodies" as used herein include polyclonal antibodies, monoclonal antibodies, antibody variants such as single chain (recombinant) Fv, human antibodies, humanized antibodies, chimeric antibodies, and immunologically active fragments of antibodies.

"Purified" antibody as used herein refers to an antibody which has been identified, separated and/or recovered from a component of its natural environment. For example, composition comprising an antibody as described herein will be purified from a cell culture or other synthetic environment to greater than 60%, 70%, 80%, 85%, 90%, 95%, 96%, 97%, 98%, or 99% by weight of the antibody.

"Binds specifically" as used herein refers to the act of an antibody binding to its antigen and is intended exclude low-level, non-specific binding that may occur between random proteins. "Binds specifically" as used herein is not intended and does not imply that the antibody will not bind to any protein other than the proteins or polypeptides as disclosed herein since antibodies can cross-react with any protein that includes the relevant epitope.

"Inverse agonist" of TSHR as used herein refers to an agent, such as an antibody, which binds to TSHR, but exerts the opposite effect of an agonist (e.g., TSH) of TSHR. For example, an inverse agonist of TSHR is an antibody that reduces ligand-independent constitutive activity of TSHR.

"Discontinuous conformational epitope" as used herein refers to non-sequential epitopes that upon protein folding, diverse regions of the antigen may come together to form the complete epitope that is recognized by the antibody.

"Mammal" as used herein refers to any member of the class Mammalia, including, without limitation, humans and non-human primates such as chimpanzees, and other apes and monkey species; farm animals such as cattle, sheep, pigs, goats and horses; domestic mammals such as dogs and cats;

laboratory animals including rodents such as mice, rats and guinea pigs, and the like. The term does not denote a particular age or sex. Thus adult and newborn subjects, as well as fetuses, whether male or female, are intended to be including within the scope of this term.

"Therapeutically effective amount" as used herein refers to that amount which is capable of achieving beneficial results in a patient with disease or disease condition for which the treatment is sought. A therapeutically effective amount can be determined on an individual basis and will be based, at least in part, on consideration of the physiological characteristics of the mammal, the type of delivery system or therapeutic technique used and the time of administration relative to the progression of the disease.

"Beneficial results" may include, but are in no way limited to, lessening or alleviating the severity of the disease condition, preventing the disease condition from worsening, curing the disease condition and prolonging a patient's life or life expectancy.

"Cancer" and "cancerous" refer to or describe the physiological condition in mammals that is typically characterized by unregulated cell growth. Examples of cancer include, but are not limited to, thyroid cancer, including papillary, follicular, medullary, and anaplastic thyroid cancer.

"Conditions" and "disease conditions," as used herein may include, but are in no way limited to any form of thyroid or thyroid-related diseases and disease conditions, including but not limited to hyperthyroidism, thyroid cancer and thyrotoxicosis.

"Pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Treatment" and "treating," as used herein refer to both therapeutic treatment and prophylactic or preventative measures, wherein the object is to prevent or slow down (lessen) the targeted pathologic condition or disorder even if the treatment is ultimately unsuccessful. Those in need of treatment include those already with the disorder as well as those prone to have the disorder or those in whom the disorder is to be prevented. For example, in thyroid cancer treatment, a therapeutic agent may directly decrease the pathology of tumor cells, or render the tumor cells more susceptible to treatment by other therapeutic agents or by the subject's own immune system.

"Tumor," as used herein refers to all neoplastic cell growth and proliferation, whether malignant or benign, and all pre-cancerous and cancerous cells and tissues.

"Substantial portion" as used herein relating to an epitope refers to a portion of the epitope that is greater than 60%, 70%, 80%, 90%, 95%, 96%, 97%, 98%, or 99% of the epitope.

"Thyrotropin receptor ("TSHR")" as used herein includes both wild-type TSHR and mutant TSHR (e.g., gain-of-function TSHR mutants).

In the course of generating a diverse panel of TSHR mAb, the inventors noted that a monoclonal antibody (mAb), "CS-17," possessed a novel feature not described previously, namely strong inverse agonist activity. In the absence of TSH, CS-17 reduces TSHR constitutive activity in vitro with a half maximal inhibitory concentration of approximately 1 µg/ml ($6.7 \times 10^{-9}$ M). Moreover, CS-17 suppresses to a similar extent a number of TSHR mutations associated with constitutive activities far higher than the wild-type TSHR. Administered to mice in vivo, CS-17 reduced serum T4 levels. CS-17 also had modest TSH blocking activity. Therefore, the inventors believe that CS-17 may be developed and used as a therapeutic agent in thyroid cancer, as well as in other selected hyperthyroidism states.

Figure 4:
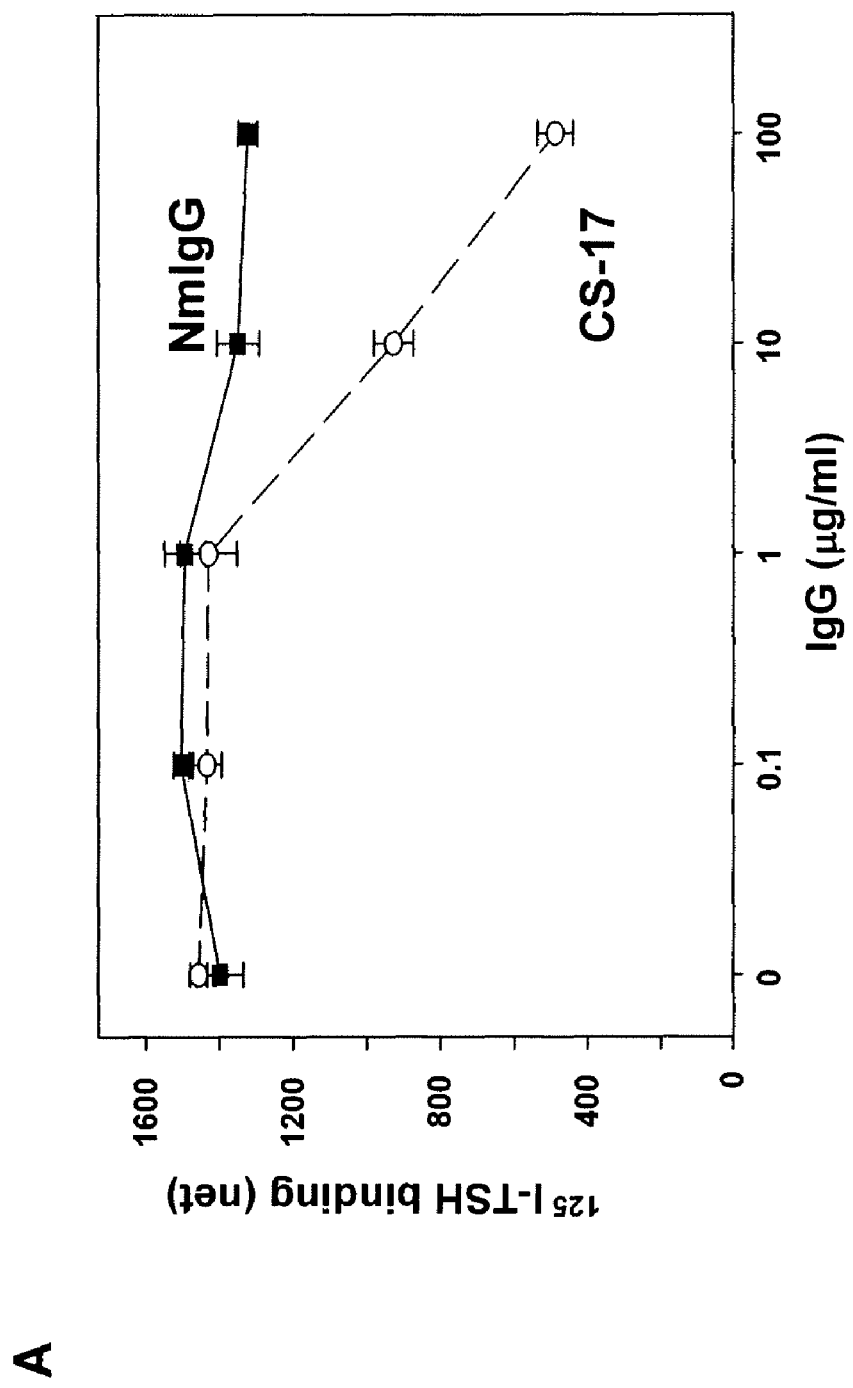
FIG. 4 depicts the effect of CS-17 on TSH binding to, and activation of, the TSHR in accordance with an embodiment of the present invention. Panel A: Cell monolayers expressing the wild-type TSHR were preincubated for 1 h at 37° C. with the indicated concentrations of CS-17 or purified normal mouse IgG (NmIgG) prior to the addition of $^{125}$I-TSH. After a further 2 h incubation at room temperature, cells were rinsed and radioactivity was measured in solubilized cells. The values shown are 'net' after subtraction of binding to cells not expressing the TSHR. Each point represents the mean±S.D. of values obtained in duplicate dishes of cells. Similar data were obtained in a separate experiment (total of ~8000 cpm $^{125}$I-TSH added per dish with 600-850 cpm subtracted to provide the net data). Panel B: Influence of CS-17 on the cAMP response to low dose TSH stimulation. COS-7 cells transiently transfected with the wild-type TSHR were incubated for 60 min in the indicated concentrations of bTSH in the absence of presence of CS-17 (10 µg/ml and 100 µg/ml). Intracellular cAMP levels in mock transfected cells (empty expression vector) were unaffected by either concentration of CS-17. Each point represents the mean of cAMP values determined in duplicate wells of cells. Panel C: Data similar to those for CS-17, but with a control TSHR mAb, 4C1.
Figure 4:
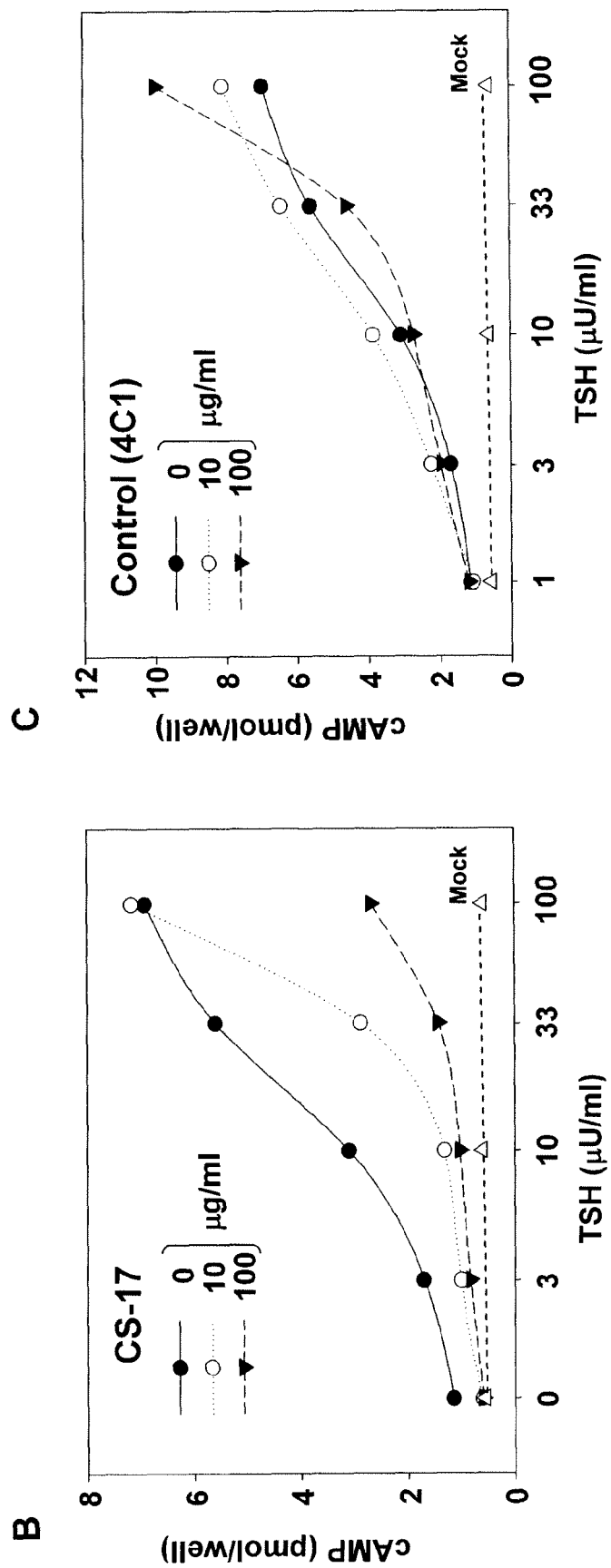

An important potential clinical use for an antibody such as CS-17 is in the treatment of thyroid cancer after thyroid ablation. Moreover, at physiological TSH levels, the CS-17 effect on TSHR constitutive activity predominates over TSH responsiveness (FIG. 4C).

The inventors have generated a TSHR mAb with the previously unrecognized property of being an inverse agonist for TSHR constitutive activity. CS-17 interacts with the large extracellular domain of the TSHR and the inventors believe that it is unique among GPCR inverse agonists. This mAb is active with TSHR mutations responsible for enhanced constitutive activity. After humanization, CS-17 may be a therapeutic agent in a number of thyroid diseases ranging from thyroid cancer to hyperthyroidism.

Furthermore, the antibodies of the present invention may also have non-therapeutic utility; for example, affinity purification of TSHR.

Various embodiments of the present invention are based these findings by the inventors.

Purified Antibodies That Bind Specifically to TSHR and have Inverse Agonist Activity on TSHR One embodiment of the present invention provides for a purified antibody that binds specifically to TSHR and has inverse agonist activity on TSHR and mutant variants of TSHR. In one embodiment, the purified antibody is a monoclonal antibody. In a particular embodiment, the purified antibody is CS-17, which is a monoclonal antibody produced by hybridoma CS-17, which was deposited at the American Type Culture Collection on Jan. 25, 2007, ATCC accession number PTA-8174. In another embodiment, the purified antibody is an antibody having the same epitope specificity as a monoclonal antibody produced by hybridoma CS-17, ATCC accession number PTA-8174. In another embodiment, the purified antibody is an antibody having substantially the same epitope specificity as a monoclonal antibody produced by hybridoma CS-17, ATCC accession number PTA-8174.

In various embodiments, the mutant variants of TSHR include S281I, I486F, I568T, A623I and V656F mutants as described herein.

In another embodiment, the purified antibody binds specifically to an epitope on TSHR. In one embodiment, the epitope is located on the α-subunit of TSHR.

In another embodiment, the purified antibody binds specifically to a conformational epitope on TSHR. In one embodiment, the purified antibody binds specifically to a conformational epitope located between amino acid residues 171 and 260 of TSHR.

In another embodiment, the purified antibody binds specifically to a conformational epitope wherein a substantial portion of the conformational epitope is located between amino acid residues 171 and 260 of TSHR.

In another embodiment, the purified antibody binds specifically to a discontinuous conformational epitope. In one embodiment, the purified antibody binds specifically to a discontinuous conformational epitope located between amino acid residues 171 and 260 of TSHR. In another embodiment, the purified antibody binds specifically to a discontinuous conformational epitope wherein a substantial portion of the discontinuous conformational epitope is located between amino acid residues 171 and 260 of TSHR.

In another embodiment, the antibody binds specifically to a polypeptide as disclosed by SEQ ID NO: 1 and has inverse agonist activity on the polypeptide. SEQ ID NO: 1 discloses an amino acid sequence of human TSHR (see also, FIG. 7). In other embodiments, the antibody binds specifically to a polypeptide at least 95%, 96%, 97%, 98% or 99% identical to SEQ ID NO: 1.

In another embodiment, the purified antibody binds specifically to a conformational epitope on a polypeptide as disclosed by SEQ ID NO: 1. In other embodiments, the purified antibody binds specifically to a conformational epitope on a polypeptide at least 95%, 96%, 97%, 98% or 99% identical to SEQ ID NO: 1.

In another embodiment, the purified antibody binds specifically to a discontinuous conformational epitope on a polypeptide as disclosed by SEQ ID NO: 1. In other embodiments, the purified antibody binds specifically to a discontinuous conformational epitope on a polypeptide at least 95%, 96%, 97%, 98% or 99% identical to SEQ ID NO: 1.

In another embodiment, the purified antibody binds specifically to a polypeptide as disclosed by SEQ ID NO: 2 and has inverse agonist activity on the polypeptide. SEQ ID NO: 2 discloses amino acid residues 171-260 of human TSHR (see also, FIG. 8). In other embodiments, the antibody binds specifically to a polypeptide at least 95%, 96%, 97%, 98% or 99% identical to SEQ ID NO: 2.

In another embodiment, the purified antibody binds specifically to a conformational epitope on TSHR that is located on SEQ ID NO: 2. In other embodiments, the purified antibody binds specifically to a conformational epitope on TSHR that located on a polypeptide at least 95%, 96%, 97%, 98% or 99% identical to SEQ ID NO: 2.

In another embodiment, the purified antibody binds specifically to a conformational epitope on TSHR wherein a substantial portion of the conformational epitope is located on SEQ ID NO: 2. In other embodiments, the purified antibody binds specifically to a conformational epitope on TSHR wherein a substantial portion of the conformational epitope is located on a polypeptide at least 95%, 96%, 97%, 98% or 99% identical to SEQ ID NO 2.

In another embodiment, the purified antibody binds specifically to a discontinuous conformational epitope on TSHR that is located on SEQ ID NO: 2. In other embodiments, the purified antibody binds specifically to a discontinuous conformational epitope on TSHR that located on a polypeptide at least 95%, 96%, 97%, 98% or 99% identical to SEQ ID NO: 2.

In another embodiment, the purified antibody binds specifically to a discontinuous conformational epitope on TSHR wherein a substantial portion of the discontinuous conformational epitope is located in SEQ ID NO: 2. In other embodiments, the purified antibody binds specifically to a discontinuous conformational epitope on TSHR wherein a substantial portion of the discontinuous conformational epitope is located on a polypeptide at least 95%, 96%, 97%, 98% or 99% identical to SEQ ID NO: 2.

In one embodiment, the purified antibody binds specifically to a polypeptide that is encoded by the polynucleotide as disclosed by SEQ ID NO: 3 and has inverse agonist activity on the polypeptide. SEQ ID NO: 3 discloses a human TSHR nucleotide coding region (see also, FIG. 9). In other embodiments, the purified antibody binds specifically to a polypeptide that is encoded by a polynucleotide at least 95%, 96%, 97%, 98% or 99% identical to SEQ ID NO: 3.

In one embodiment, the purified antibody binds specifically to a conformational epitope on a polypeptide that is encoded by the polynucleotide as disclosed by SEQ ID NO: 3. In other embodiments, the purified antibody binds specifically to a conformational epitope on a polypeptide that is encoded by a polynucleotide at least 95%, 96%, 97%, 98% or 99% identical to SEQ ID NO: 3.

In one embodiment, the purified antibody binds specifically to a discontinuous conformational epitope on a polypeptide that is encoded by the polynucleotide as disclosed by SEQ ID NO: 3. In other embodiments, the purified antibody binds specifically to a discontinuous conformational epitope on a polypeptide that is encoded by a polynucleotide at least 95%, 96%, 97%, 98% or 99% identical to SEQ ID NO: 3.

In another embodiment, the purified antibody binds specifically to a polypeptide that is encoded by the polynucleotide as disclosed by SEQ ID NO: 4 and has inverse agonist activity on the polypeptide. SEQ ID NO: 4 discloses a human TSHR nucleotide coding region for amino acid residues within residues 171-260 of TSHR. In other embodiments, the purified antibody binds specifically to a polypeptide that is encoded by a polynucleotide at least 95%, 96%, 97%, 98% or 99% identical as SEQ ID NO: 4.

In another embodiment, the purified antibody binds specifically to a conformational epitope that is located on a polypeptide encoded by the polynucleotide as disclosed by SEQ ID NO: 4. In other embodiments, the purified antibody binds specifically to a conformational epitope that is located on a polypeptide encoded by a polynucleotide at least 95%, 96%, 97%, 98% or 99% identical to SEQ ID NO: 4.

In another embodiment, the purified antibody binds specifically to a conformational epitope on TSHR wherein a substantial portion of the conformational epitope is located on a polypeptide encoded by the polynucleotide as disclosed by SEQ ID NO: 4. In other embodiments, the purified antibody binds specifically to a conformational epitope on TSHR wherein a substantial portion of the conformational epitope is located on a polypeptide encoded by a polynucleotide at least 95%, 96%, 97%, 98% or 99% identical to SEQ ID NO: 4.

In another embodiment, the purified antibody binds specifically to a discontinuous conformational epitope that is located on a polypeptide encoded by the polynucleotide as disclosed by SEQ ID NO: 4. In other embodiments, the purified antibody binds specifically to a discontinuous conformational epitope that located on a polypeptide encoded by a polynucleotide at least 95%, 96%, 97%, 98% or 99% identical to SEQ ID NO: 4.

In another embodiment, the purified antibody binds specifically to a discontinuous conformational epitope on TSHR wherein a substantial portion of the discontinuous conformational epitope is located on a polypeptide encoded by the polynucleotide as disclosed by SEQ ID NO: 4. In other embodiments, the purified antibody binds specifically to a discontinuous conformational epitope on TSHR wherein a substantial portion of the discontinuous conformational epitope is located on a polypeptide encoded by a polynucleotide at least 95%, 96%, 97%, 98% or 99% identical to SEQ ID NO: 4.

One of skill in the art will be able to produce the antibodies described herein without undue experimentation in light of the disclosure herein, including the examples.

Methods of preparing monoclonal antibodies are known in the art. For example, monoclonal antibodies may be prepared using hybridoma methods, such as those described by Kohler and Milstein (1975) *Nature* 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include TSHR or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (see pp. 59-103 in Goding (1986) *Monoclonal Antibodies: Principles and Practice* Academic Press). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In another embodiment the antibodies to an epitope for TSHR, a conformational epitope for TSHR, or a discontinuous conformational epitope for TSHR as described herein or a fragment thereof are humanized antibodies. Humanized forms of non-human (e.g., murine) antibodies are chimeric molecules of immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al. 1986. *Nature* 321:522-525; Riechmann et al. 1988. *Nature* 332:323-329; Presta. 1992. *Curr. Op. Struct. Biol.* 2:593-596). Humanization can be essentially performed following methods of Winter and co-workers (see, e.g., Jones et al. 1986. *Nature* 321:522-525; Riechmann et al. 1988. *Nature* 332:323-327; and Verhoeyen et al. 1988. *Science* 239:1534-1536), by substituting rodent CDRs or CDR sequences for the corresponding sequences of a human antibody. Accordingly, such humanized antibodies are chimeric antibodies (e.g., U.S. Pat. No. 4,816,567), wherein substantially less than an intact human variable domain has been substituted by the corresponding sequence from a non-human species.

In another embodiment the antibodies to an epitope for TSHR, a conformational epitope for TSHR, or a discontinuous conformational epitope for TSHR as described herein or a fragment thereof are human antibodies. Human antibodies can also be produced using various techniques known in the art, including phage display libraries (Hoogenboom and Winter. 1991. *J. Mol. Biol.* 227:381-388; Marks et al. 1991. *J. Mol. Biol.* 222:581-597) or the preparation of human monoclonal antibodies (e.g., Cole et al. 1985. *Monoclonal Antibodies and Cancer Therapy* Liss; Boerner et al. 1991. *J. Immunol.* 147(1):86-95). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in most respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al. 1992. *Bio/Technology* 10:779-783; Lonberg et al. 1994. *Nature* 368:856-859; Morrison. 1994. *Nature* 368:812-13; Fishwild et al. 1996. *Nature Biotechnology* 14:845-51; Neuberger. 1996. *Nature Biotechnology* 14:826; Lonberg and Huszar. 1995. *Intern. Rev. Immunol.* 13:65-93. U.S. Pat. No. 6,719,971 also provides guidance to methods of generating humanized antibodies.

Hybridomas that Produce an Antibody that Binds Specifically to TSHR and has Inverse Agonist Activity on TSHR Other embodiments of the present invention provide for a hybridoma that produces a purified antibody, as described herein, that binds specifically to TSHR and has inverse agonist activity on TSHR. One of skill in the art will be able to produce and screen for the hybridomas described herein without undue experimentation in light of the disclosure herein, including the examples.

In one embodiment, the present invention provides for a cell of hybridoma CS-17, which was deposited at the American Type Culture Collection (ATCC) on Jan. 25, 2007, ATCC accession number PTA-8174. The address of ATCC is 10801 University Blvd., Manassas, Va. 20110-2209, USA.

Methods of Using a Purified Antibody that Binds Specifically to TSHR and has Inverse Agonist Activity on TSHR to Treat a Thyroid Disease, Thyroid-Related Disease or Disease Condition Another embodiment of the present invention provides for a method of using a purified antibody that binds specifically to TSHR and has inverse agonist activity on TSHR to treat a thyroid or thyroid-related disease or disease condition. The method may be a primary therapeutic therapy or an adjunctive therapy in the treatment of the thyroid or thyroid-related disease or disease condition.

In one embodiment, the method may comprise providing a purified antibody that binds specifically to TSHR and has inverse agonist activity on TSHR as described herein and administering a therapeutically effective amount of the purified antibody to a mammal in need of treatment for the thyroid or thyroid-related disease or disease condition.

Another embodiment of the present invention provides for a method to treat thyroid cancer. The method may comprise providing a purified antibody that binds specifically to TSHR and has inverse agonist activity on TSHR as described herein and administering a therapeutically effective amount of the purified antibody to a mammal in need of treatment for thyroid cancer. In a particular embodiment, the mammal is human. In another embodiment, administering the purified antibody may comprise administering the purified antibody after surgical removal of thyroid carcinoma and/or radio-iodine ablation of residual thyroid cells. In another embodiment, administering the purified antibody may comprise administering the purified antibody concurrently with treatment for radio-iodine ablation of residual thyroid cells.

Another embodiment of the present invention provides for a method of treating hyperthyroidism. The method may comprise providing a purified antibody that binds specifically to TSHR and has inverse agonist activity on TSHR as described herein and administering a therapeutically effective amount of the purified antibody to a mammal in need of treatment for hyperthyroidism.

The therapeutically effective amount of the purified antibody that binds specifically to TSHR and has inverse agonist activity on TSHR may depend on a variety of factors.

The precise therapeutically effective amount may be an amount of the purified antibody that binds specifically to TSHR and has inverse agonist activity on TSHR that will yield the most effective results in terms of efficacy of treatment in a given subject. This amount will vary depending upon a variety of factors, including but not limited to the characteristics of the therapeutic antibody (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation (if used), and the route of administration. One skilled in the clinical and pharmacological arts will be able to determine a therapeutically effective amount through routine experimentation, for instance, by monitoring a subject's response to administration of the antibody and adjusting the dosage accordingly.

Typical dosages of an effective amount of the purified antibody that binds specifically to TSHR and has inverse agonist activity on TSHR can be indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tissues, or the responses observed in the appropriate animal models, as previously described.

In various embodiments, the therapeutically effective amount may be about 1 μg to about 2500 μg of a purified antibody that binds specifically to TSHR and has inverse agonist activity on TSHR. In various particular embodiments, the therapeutically effective amount may be about 1 μg to about 25 μg, about 25 μg to about 250 μg or about 250 μg to about 2500 μg. In one particular embodiment, the therapeutically effective amount may be about 250 μg.

In another embodiment, the therapeutically effective amount may be an amount that will bring a serum level to at least 0.01 μg/ml of the purified antibody that binds specifically to TSHR and has inverse agonist activity on TSHR. In various embodiments, the therapeutically effective amount may be an amount that will bring a serum level to about 0.01 μg/ml to about 250 μg/ml, about 0.01 μg/ml to about 1 μg/ml, about 1 μg/ml to about 10 μg/ml, about 10 μg/ml to about 100 μg/ml, or about 100 μg/ml to about 250 μg/ml. In various embodiments, the therapeutically effective amount may be an amount that brings serum levels to about 1 μg/ml, 5 μg/ml, 10 μg/ml, 20 μg/ml, 30 μg/ml, 40 μg/ml, 50 μg/ml, 60 μg/ml, 70 μg/ml, 80 μg/ml, 90 μg/ml or 100 μg/ml.

Methods of Making a Purified Antibody that Binds Specifically to TSHR and Has Inverse Agonist Activity on TSHR Additional embodiments of the present invention provide for methods of making a purified antibody that binds specifically to TSHR and has inverse agonist activity on TSHR. In one embodiment, the method comprises providing a hybridoma cell that produces a monoclonal antibody that binds specifically to TSHR and has inverse agonist activity on TSHR, and culturing the cell under conditions that permit the production of the monoclonal antibody.

In a particular embodiment, the hybridoma cell is a cell of hybridoma CS-17, which was deposited at the American Type Culture Collection (ATCC) on Jan. 25, 2007, ATCC accession number PTA-8174. The address of ATCC is 10801 University Blvd., Manassas, Va. 20110-2209, USA.

Kits

Another embodiment of the present invention provides for a kit for using a purified antibody that binds specifically to TSHR and has inverse agonist activity on TSHR to treat a thyroid disease, thyroid-related disease or disease condition. The kit is useful for practicing the inventive method of treating a thyroid disease or disease condition. The kit is an assemblage of materials or components, including at least one of the inventive antibodies. Thus, in some embodiments the kit contains a composition including a purified antibody that binds specifically to TSHR and has inverse agonist activity on TSHR as described herein.

The exact nature of the components configured in the inventive kit depends on its intended purpose. For example, some embodiments are configured for the purpose of treating a thyroid disease, thyroid-related disease or disease condition. In some embodiments, the kits are configured for the purpose of treating thyroid cancer. In other embodiments the kit is configured for the purpose of treating hyperthyroidism. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat a thyroid disease or disease condition, including but not limited to thyroid cancer, hyperthyroidism and thyrotoxicosis. Optionally, the kit also contains other useful components, such as, pharmaceutically acceptable carriers, syringes, catheters, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in antibody therapy. As used herein, the term "package" refers to a suitable solid matrix or material such as glass, plastic, paper, foil, and the like, capable of holding the individual kit components. Thus, for example, a package can be a glass vial used to contain suitable quantities of a purified antibody that binds specifically to TSHR and has inverse agonist activity on TSHR as described herein. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

TSHR Monoclonal Antibodies

Monoclonal antibody CS-17 is one of a panel of TSHR mAb generated by the inventors from seven fusions over a three year period. In brief, 6- to 8-week-old female BALB/c mice (The Jackson Laboratory, Bar Harbor, Me.) were injected intramuscularly with adenovirus expressing the human TSHR A-subunit, as reported previously (Chen et al. 2003. The thyrotropin receptor autoantigen in Graves' disease is the culprit as well as the victim. *J. Clin. Invest* 111: 1897-1904; Chen et al. 2004. Low-dose immunization with adenovirus expressing the thyroid-stimulating hormone receptor A-subunit deviates the antibody response toward that of autoantibodies in human Graves' disease. *Endocrinol.* 145:228-233.). Three days before fusion, mice were boosted intravenously with 50 μg of affinity-purified TSHR A subunit protein generated in Chinese hamster ovary (CHO) cells (Chazenbalk et al. 1997. Engineering the human thyrotropin receptor ectodomain from a non-secreted form to a secreted, highly immunoreactive glycoprotein that neutralizes autoantibodies in Graves' patients' sera. *J. Biol. Chem.* 272:18959-18965.). Mouse splenocytes were fused to murine SP-2/0 cells (American Type Culture Collection, Rockville, Md.) using 50% polyethylene glycol (Sigma, St. Louis Mo.). Hybridoma selection was by standard techniques using hypoxanthine, aminopterin and thymidine (HAT) in Dulbecco's modified medium (DMEM; Invitrogen, Carlsbad Calif.) containing 10% fetal bovine serum, gentamycin, L-glutamine and sodium pyruvate. Approximately two weeks after fusion, culture supernatants secreting IgG (ELISA from Bethyl, Montgomery Tex.) were screened by flow cytometry using TSHR-expressing CHO cells. Hybridomas of interest were recloned three times by limiting dilution to obtain the monoclonal cell lines. For IgG purification, cells were cultured in serum-free medium and the latter applied to Protein G Hi-Trap columns (Pharmacia, now GE Healthcare, Piscataway N.J.). Non-functional murine mAb 4C1 (Johnstone et al. 2003. A functional site on the human TSH receptor: a potential therapeutic target in Graves' disease. *Clin. Endocrinol. (Oxf)* 59:437-441.) was purchased from Serotec, Oxford, U.K.

Example 2

Construction and Expression of TSHR Mutants

Construction of TSHR mutations C24,29S, C24,31S and C29,31S in the mammalian expression vector pECE-NEO (Nagayama et al. 1989. Molecular cloning, sequence and functional expression of the cDNA for the human thyrotropin receptor. *Biochem. Biophys. Res. Comm.* 165:1184-1190.) has been reported previously (Chen et al. 2001. A full biological response to autoantibodies in Graves' disease requires a disulfide-bond loop in the thyrotropin N-terminus homologous to a laminin EGF-like domain. *J. Biol. Chem.* 276: 14767-14772.). Chimeric TSH-luteinizing hormone receptors (TSH-LHR) in the vector pECE-neo were also reported previously (Nagayama et al. 1991. Thyrotropin-luteinizing hormone/chorionic gonadotropin receptor extracellular domain chimeras as probes for TSH receptor function. *Proc. Natl. Acad. Sci. U.S.A.* 88:902-905.). Of these, TSH-LHR-6, TSH-LHR-9 and TSH-LHR-10 (depicted schematically in the figures) required additional modification to convert the histidine 601 polymorphism (Nagayama et al. 1989. Molecular cloning, sequence and functional expression of the cDNA for the human thyrotropin receptor. *Biochem. Biophys. Res. Comm.* 165:1184-1190.) to tyrosine (H601Y) (Biebermann et al. 1998. A conserved tyrosine residue (Y601) in transmembrane domain 5 of the human thyrotropin receptor serves as a molecular switch to determine G-protein coupling. *FASEB J.* 12:1461-1471.) and to delete the 5'- and 3'-untranslated ends (Kakinuma et al. 1996. Both the 5' and 3' non-coding regions of the thyrotropin receptor messenger RNA influence the level of receptor protein expression in transfected mammalian cells. *Endocrinol.* 137:2664-2669.). Gain-of-function TSHR mutants S281 I (Kopp et al. 1997. Congenital hyperthyroidism caused by a solitary toxic adenoma harboring a novel somatic mutation (Serine281-Isoleucine) in the extracellular domain of the thyrotropin receptor. *J. Clin. Invest.* 100:1634-1639.), I486F and I568T (Parma et al. 1995. Somatic mutations causing constitutive activity of the thyrotropin receptor are the major cause of hyperfunctioning thyroid adenomas: Identification of additional mutations activating both the cyclic adenosine 3',5'-monophosphate and inositol phosphate-Ca2+ cascades. *Mol. Endocrinol.* 9:725-733.), A623I (Parma et al. 1993. Somatic mutations in the thyrotropin receptor gene cause hyperfunctioning thyroid adenomas. *Nature* 365:649-651.) and V656F (Fuhrer et al. 1997. Somatic mutations in the thyrotropin receptor gene and not in the Gs alpha protein gene in 31 toxic thyroid nodules. *J. Clin. Endocrinol. Metab* 82:3885-3891.) were introduced into the wild-type TSHR in the same vector using the Quick-Change site-directed mutagenesis kit (Stratagene, San Diego, Calif.). Plasmids were transiently expressed in Cos-7 cells using FuGENE6 (Roche, Indianapolis, Ind.). Cells were cultured in DMEM supplemented with 10% fetal calf serum, penicillin (100 U/ml), gentamycin (50 μg/ml) and fungizone (2.5 μg/ml) and were tested 48 h after transfection.

Example 3

Cultured Cell cAMP Assays

COS-7 cells expressing the wild-type TSHR and TSHR mutants were transferred into 96-well plates 24 hours after transfection and 24 hours prior to assay. Cells from the same transfection were also plated in 6 cm culture dishes to monitor the transfection efficiency by flow cytometry (see below). For bioassay, cells were incubated in DMEM medium supplemented with 1 mM isobutyl methylanthine (IBMX) and 10 mM HEPES). Where indicated in the text, media also contained purified mAb CS-17 or bovine (b) TSH (Sigma). Purified normal mouse IgG and mock transfected COS-7 cells were included as controls. After 60 min at 37° C., the medium was aspirated and intracellular cAMP was extracted with 0.2 ml 95% ethanol. The extracts were evaporated to dryness, resuspended in 0.1 ml of Dulbecco's phosphate-buffered saline (PBS), pH 7.5, and samples (20 μl) were assayed using the LANCE cAMP kit according to the protocol of the manufacturer (PerkinElmer, Shelton Conn.).

Example 4

Flow Cytometry

Transiently transfected COS-7 cells were harvested from 6 cm diameter dishes using 1 mM EDTA, 1 mM EGTA in PBS. After washing twice with PBS containing 10 mM HEPES, pH 7.4, 2% fetal bovine serum, and 0.05% NaN3, the cells were incubated for 30 min at room temperature in 100 μl of the same buffer containing 1 μg of either normal mouse IgG, mAb CS-17, or mAb 2C11. After rinsing, the cells were incubated for 45 min with 100 μl fluorescein isothiocyanate-conjugated goat anti-mouse IgG (1:100) (Caltag, Burlingame, Calif.), washed, and analyzed using a Beckman FAC-Scan flow cytofluorimeter. Cells stained with propidium iodide (1 μg/ml final concentration) were excluded from analysis. For determining CS-17 blood concentrations following mAb injections in vivo, the inventors performed flow cytometry using intact CHO cells stably expressing the wild-type TSHR and, as standards, normal mouse serum supplemented with different amounts of CS-17.

Example 5

TSH Binding to Transfected Cells

COS-7 cells transiently transfected with plasmids expressing the wild-type TSHR or TSHR mutants were grown to confluence in 24-well plates. Medium was aspirated and replaced with 250 μl binding buffer (Hanks' buffer with 250 mM sucrose substituting for NaCl to maintain isotonicity and 0.25% bovine serum albumin) containing ~8,000 cpm $^{125}$I-TSH (Kronus, Boise, Id.). After incubation for 1-2 h at room temperature, cells were rapidly rinsed three times with binding buffer (4° C.), solubilized with 0.5 ml 1 N NaOH, and radioactivity was then measured in a g-counter. Non-specific binding was determined using COS-7 cells transfected in parallel with the vector alone. In some experiments, cells were preincubated for 1 h at 37° C. in DMEM containing 10% fetal calf serum and the indicated concentrations of CS-17 prior to replacement of the medium with binding buffer containing $^{125}$I-TSH and the same CS-17 concentration.

Example 6

In Vivo Study of TSHR Monoclonal Antibody CS-17

Purified CS-17 or normal mouse IgG (250 μg) in sterile PBS were injected intraperitoneally into 6-8 week-old female BALB/c mice (Jackson). Injections were administered on days 2 and 5, and blood was collected on days 1, 4 and 7. Serum total thyroxine (T4) levels were measured in undiluted serum (25 μl) by radioimmunoassay using a kit (Diagnostic Products Corp., Los Angeles, Calif.). Sera were also used to estimate CS-17 concentrations by flow cytometry. These animal studies were approved by the Institutional Animal Care and Use Committee and performed with the highest standards of animal care in a pathogen-free facility.

Example 7

Statistical Analyses

Student's t-test was used to determine the significance of differences in intracellular cAMP levels in cells treated with or without CS-17, as well as the significance of differences of T4 levels in mice injected with either normal mouse IgG or TSHR mAb CS-17.

Example 8

Characterization of TSHR Monoclonal Antibody CS-17

Figure 5:
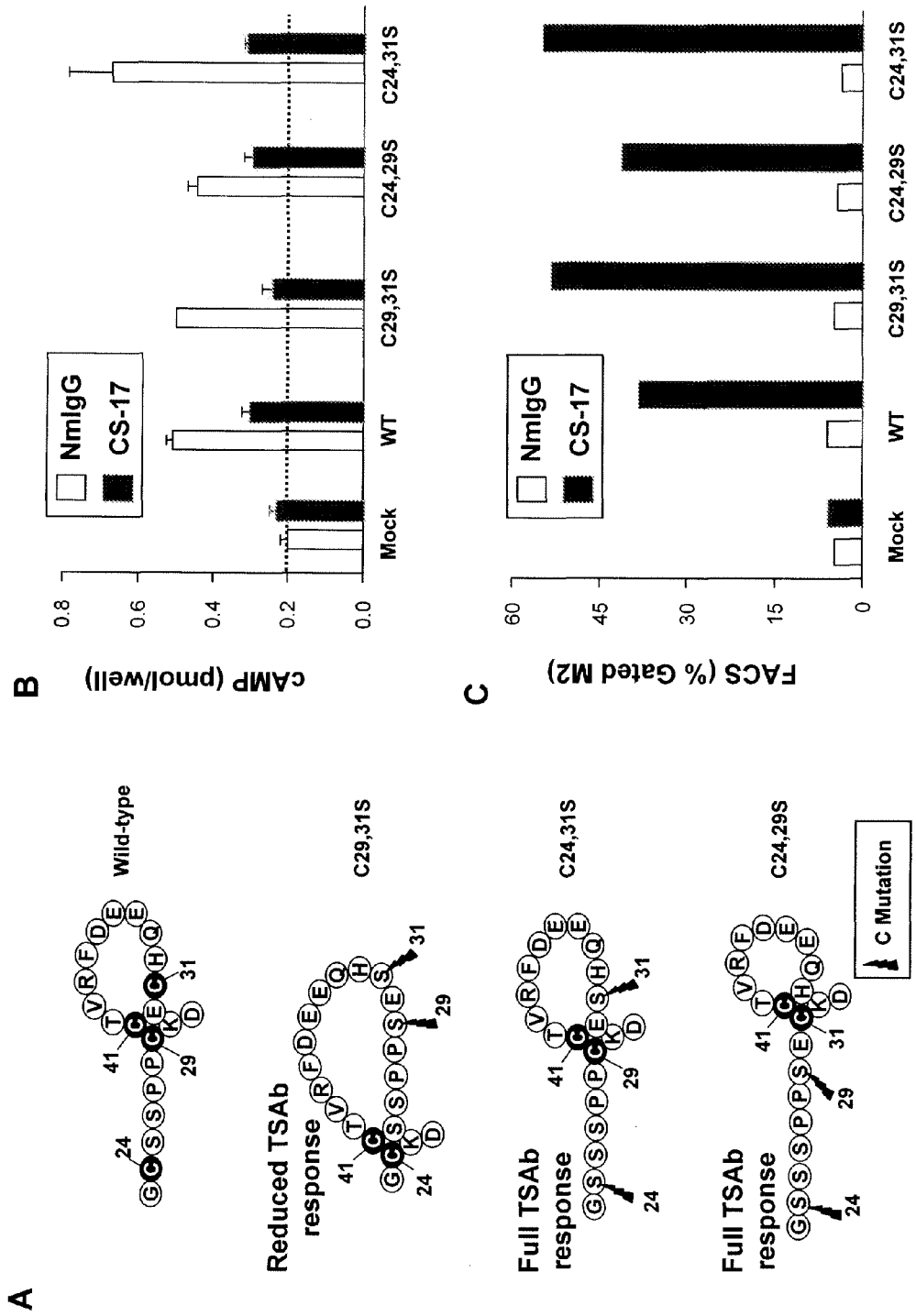
FIG. 5 depicts CS-17 inverse agonist activity as being unrelated to the TSHR N-terminal cysteine cluster important for thyroid stimulating autoantibody (TSAb) responsiveness in accordance with an embodiment of the present invention. Panel A: Schematic representation of three selected TSHR mutant in which pairs of Cys residues in the N-terminus cluster (C24, C29, C31 and C41) were converted to Ser (arrows), leaving only the remaining two Cys residues available for disulfide bridging (Chen et al. 2001. A full biological response to autoantibodies in Graves' disease requires a disulfide-bond loop in the thyrotropin N-terminus homologous to a laminin EGF-like domain. *J. Biol. Chem.* 276:14767-14772.). TSHR mutants C24,31S and C24,29S were fully responsive to TSAb, similar to the wild-type TSHR. In contrast, TSHR C29,31S (forcing a C41-C24 disulfide bond) was poorly responsive to TSAb while retaining a normal response to TSH stimulation (Chen et al. 2001. A full biological response to autoantibodies in Graves' disease requires a disulfide-bond loop in the thyrotropin N-terminus homologous to a laminin EGF-like domain. *J. Biol. Chem.* 276:14767-14772.). Panel B. Constitutive intracellular cAMP levels in aliquots of the same cells used for flow cytometry. Cells were incubated for 60 min in medium supplemented with mAb CS-17 or purified normal mouse IgG (both at 10 µg/ml) prior to cAMP extraction. Bars indicate the mean+range of values obtained in duplicate wells of cells. Similar data were observed in a separate experiment. Panel C: Flow cytometry (FACS) of mock transfected cells and TSHR transfected cells subjected to flow cytometry with mAb CS-17 and purified normal mouse IgG (both at 10 µg/ml).

Among the TSHR mAb that the inventors isolated, CS-17, an IgG2a, recognized the wild type TSHR expressed on COS-7 cells as detected by flow cytometry (FIG. 1A). Although CS-17 lacked thyroid stimulating activity, the inventors noted a novel property for a TSHR mAb, namely inverse agonist activity. The TSHR is 'noisy' in the absence of ligand (TSH), as reflected by increased intracellular cAMP levels in TSHR-expressing relative to mock-transfected COS-7 cells (FIG. 1B). TSHR mAb CS-17, at a concentration of 10 μg/ml, significantly reduced this constitutive activity (p=0.0052). As a control, another TSHR mAb (4C1) (Johnstone et al. 2003. A functional site on the human TSH receptor: a potential therapeutic target in Graves' disease. *Clin. Endocrinol. (Oxf)* 59:437-441) had no effect on TSHR constitutive activity. CS-17 did not alter cAMP levels in mock-transfected cells (FIG. 1C). Inverse agonist activity on TSHR constitutive activity was evident at a concentration of 0.1 μg/ml and was near complete at 100 μg/ml (FIG. 1C). At intermediate concentrations, CS-17 inverse agonist activity varied in different experiments, but was typically 60-90% at 10 μg/ml (see also FIGS. 4 and 5).

Example 9

CS-17 Suppresses Gain-of-Function TSHR Mutations

TSHR gain-of-function mutations are associated with autonomously functioning thyroid adenomas (Parma et al. 1993. Somatic mutations in the thyrotropin receptor gene cause hyperfunctioning thyroid adenomas. *Nature* 365:649-651.) and non-autoimmune autosomal dominant hyperthyroidism (Duprez et al. 1994. Germline mutations in the thyrotropin receptor gene cause non-autoimmune autosomal dominant hyperthyroidism. *Nature Genet.* 7:396-401.). Because these mutant TSHR have far greater constitutive activity than the wild-type TSHR, the inventors examined whether mAb CS-17 maintained its suppressive property with the former. The inventors generated and tested the effect of CS-17 on gain-of-function mutations known to involve different regions of the TSHR ectodomain accessible to antibody in intact cells, namely the hinge region (S281I) and all three extracellular loops (I486F, I568T and V656F). As a control, the inventors included a gain of function mutation in the third intracellular loop (A623I) that would not be accessible to antibody.

Figure 2:
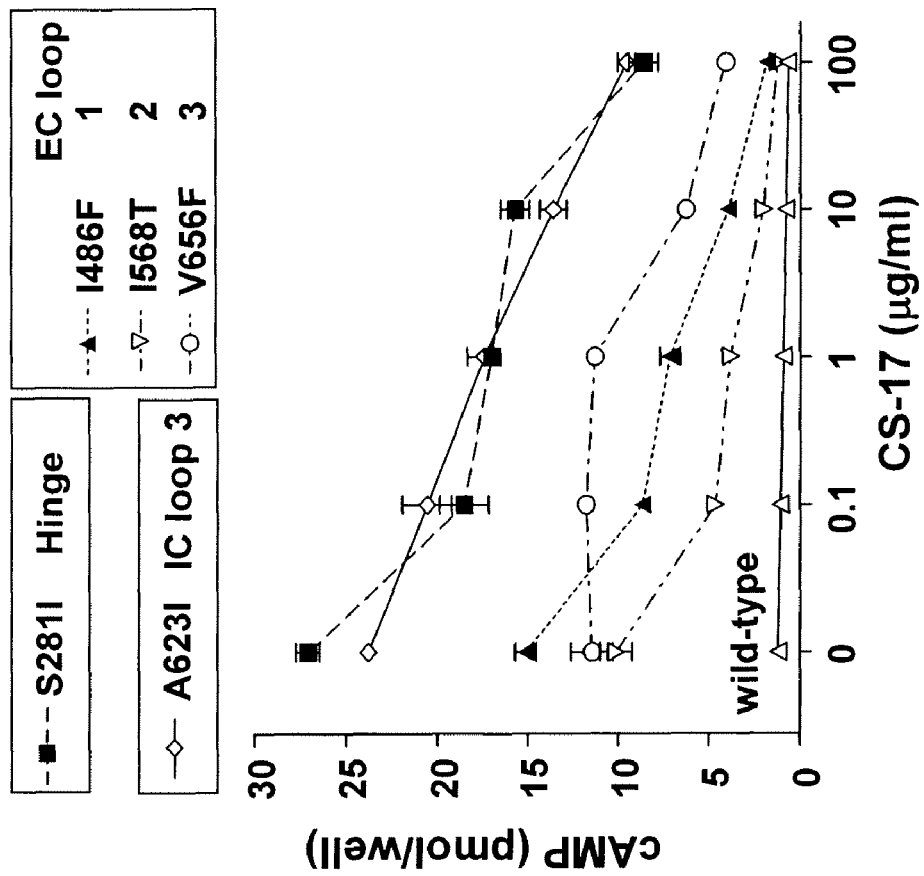
FIG. 2 depicts CS-17 suppression of gain-of-function TSHR mutations in accordance with an embodiment of the present invention. Plasmids expressing the wild-type TSHR or the indicated TSHR activating mutations were transiently transfected into COS-7 cells. After two days, cells were incubated for 1 h in control medium or in medium supplemented with the indicated CS-17 concentrations. Intracellular cAMP levels were determined in duplicate wells of cells. Bars indicate the range of duplicate values. These data are representative of three experiments. Note that because of the high degree of activity of the mutants, suppression of wild-type TSHR constitutive activity is less perceptible on the graph.

In confirmation of previous reports (Kopp et al. 1997. Congenital hyperthyroidism caused by a solitary toxic adenoma harboring a novel somatic mutation (Serine281-Isoleucine) in the extracellular domain of the thyrotropin receptor. *J. Clin. Invest.* 100:1634-1639. Parma et al. 1995. Somatic mutations causing constitutive activity of the thyrotropin receptor are the major cause of hyperfunctioning thyroid adenomas: Identification of additional mutations activating both the cyclic adenosine 3',5'-monophosphate and inositol phosphate-Ca2+ cascades. *Mol. Endocrinol.* 9:725-733; Parma et al. 1993. Somatic mutations in the thyrotropin receptor gene cause hyperfunctioning thyroid adenomas. *Nature* 365:649-651; Fuhrer et al. 1997. Somatic mutations in the thyrotropin receptor gene and not in the Gs alpha protein gene in 31 toxic thyroid nodules. *J. Clin. Endocrinol. Metab* 82:3885-3891), all of these mutations greatly increased TSHR constitutive activity, the most potent of these being S281I and A623I (FIG. 2). Despite these high levels of activity, CS-17 partially suppressed all mutant receptors including A623I that cannot be directly contacted by CS-17. CS-17 concentrations producing half-maximal inhibition (IC50) were similar to those for the wild-type TSHR (FIG. 1C), approximately 1 µg/ml, with the exception of V656F which was less sensitive to CS-17 inhibition.

Example 10

CS-17 Suppresses Thyroid Function In Vivo

Figure 3:
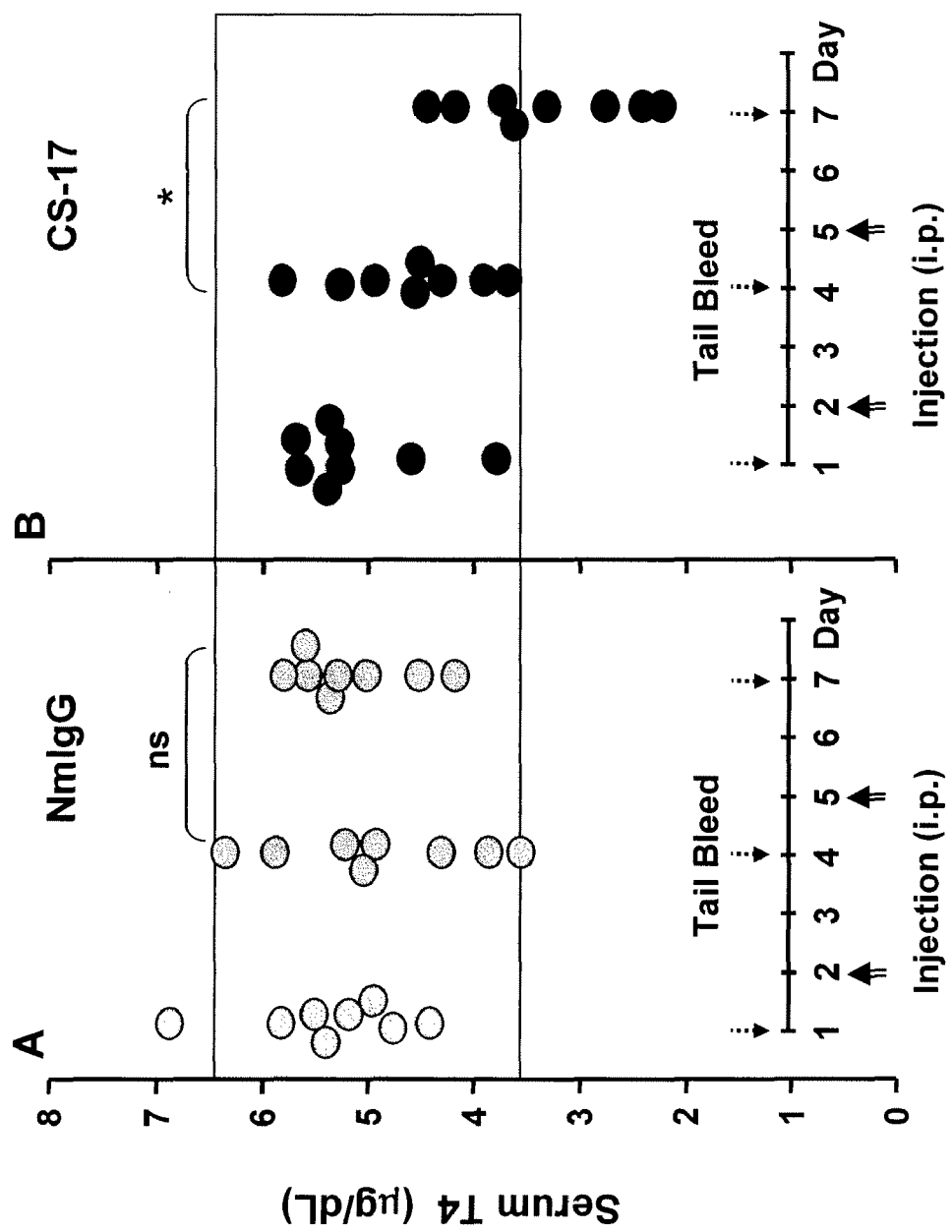
FIG. 3 depicts CS-17 suppression of thyroid function in vivo in accordance with an embodiment of the present invention. BALB/c mice were injected intra-peritoneally (i.p.) on the indicated days with 250 µg of either normal mouse IgG (NmIgG) or mAb CS-17 (8 mice in each group). Serum total T4 levels were determined on serum obtained prior to the first injection (day 1) and then 2 days after each injection (days 4 and 7). *p<0.001, Student's t test. The same phenomenon was observed in three separate experiments.

The inventors examined whether the in vitro effect of mAb CS-17 would be reflected in vivo. BALB/c mice were injected intra-peritoneally twice at a three day interval with 250 µg of either normal mouse IgG or mAb CS-17 (8 mice in each group). CS-17 concentrations in serum were estimated by flow cytometric analysis of CHO cells expressing the wild-type TSHR using a standard curve of known concentrations of CS-17 added to normal mouse serum. Serum CS-17 levels after the first and second injections were 127±5 and 232±20 µg/ml (mean±SEM; n=8), respectively. Serum total T4 levels one day prior to the first injection were 5.2±0.17 µg/dL (mean±SEM; n=16) (FIG. 3). Two days after the second injection, serum T4 was significantly lower in the mice receiving CS-17 (3.3±0.3) than in the animals receiving NmIgG (5.2±0.2) (p<0.001). Similar suppression of serum T4 levels by CS-17 was observed in three separate experiments.

Example 11

CS-17 Reduces TSH Binding to and Activation of the TSHR

In addition to suppressing TSHR ligand independent activity, CS-17, unlike purified, normal mouse IgG, inhibited $^{125}$I-TSH binding to the human TSHR expressed on the surface of cell monolayers (FIG. 4A). However, CS-17 was less potent in inhibiting TSH binding than in suppressing constitutive activity. At 10 µg/ml, CS-17 suppressed TSH binding by approximately 35% whereas the same concentration reduced constitutive activity of the wild-type TSHR by at least 60% (e.g., FIG. 1C).

With TSHR expressing cell monolayers, CS-17 at 10 µg/ml also reduced the cAMP response to TSH stimulation, but only at TSH concentrations below 100 µU/ml (FIG. 4B). TSH at 100 µU/ml, a near maximal stimulatory concentration, 'broke through' CS-17 suppression, inducing a cAMP response similar to that in the absence of CS-17. However, a ten-fold increase in CS-17 to 100 µg/ml (approximately the concentration attained in blood in the in vivo experiments), was able to partially suppress the cAMP response to this high TSH concentration. Unlike CS-17, similar concentrations of TSHR mAb 4C1 (10 and 100 µg/ml) used as a control did not suppress the cAMP response to even weak TSH stimulation (10 µU/ml) (FIG. 4C).

Example 12

Site of Action of mAb CS-17

Monoclonal antibody CS-17 was generated by immunizing mice with the major component of the TSHR A-subunit (amino acid residues 1-289). Consequently, the CS-17 epitope cannot involve TSHR ectodomain residues downstream residue 289, including the hinge region. CS-17 did not recognize an overlapping series of synthetic TSHR ectodomain peptides (data not shown), indicating that its epitope is conformational and possibly discontinuous. The inventors therefore explored CS-17 recognition of selected conformationally intact TSHR mutants expressed on the surface of transfected cells.

Previously, the inventors observed that the cysteine-rich N-terminal region of the TSHR ectodomain contributed to thyroid stimulating autoantibody (but not TSH) binding and function (Nagayama and Rapoport. 1992. Thyroid stimulatory autoantibodies in different patients with autoimmune thyroid disease do not all recognize the same components of the human thyrotropin receptor: selective role of receptor amino acids Ser25-Glu30. *J. Clin. Endocrinol. Metab.* 75:1425-1430; Chazenbalk et al. 2001. A "prion-like" shift between two conformational forms of a recombinant thyrotropin receptor A subunit module: Purification and stabilization using chemical chaperones of the form reactive with Graves' autoantibodies. *J. Clin. Endocrinol. Metab.* 86:1287-1293.). Further, by mutating permutations of cysteine residue pairs among the four cysteines (C24, C29, C31 and C41), the inventors deduced that a disulfide bond involving C41 with either C29 or C31 was necessary for TSAb responsiveness comparable to the wild-type TSHR (schematically represented in FIG. 5A) (Chen et al. 2001. A full biological response to autoantibodies in Graves' disease requires a disulfide-bond loop in the thyrotropin N-terminus homologous to a laminin EGF-like domain. *J. Biol. Chem.* 276:14767-14772.). They therefore examined whether CS-17 suppression of TSHR constitutive activity was related to this TSAb-critical region. This was not the case (FIG. 5B). Strong, similar CS-17 inverse agonist activity was evident with the TSHR mutation associated with reduced TSAb responsiveness (C29,31S) in comparison to the wild-type TSHR and TSHR mutants fully responsive to TSAb (C24,31S and C24, 29S). All TSHR mutants expressed well on the cell surface (FIG. 5C).

Figure 6:
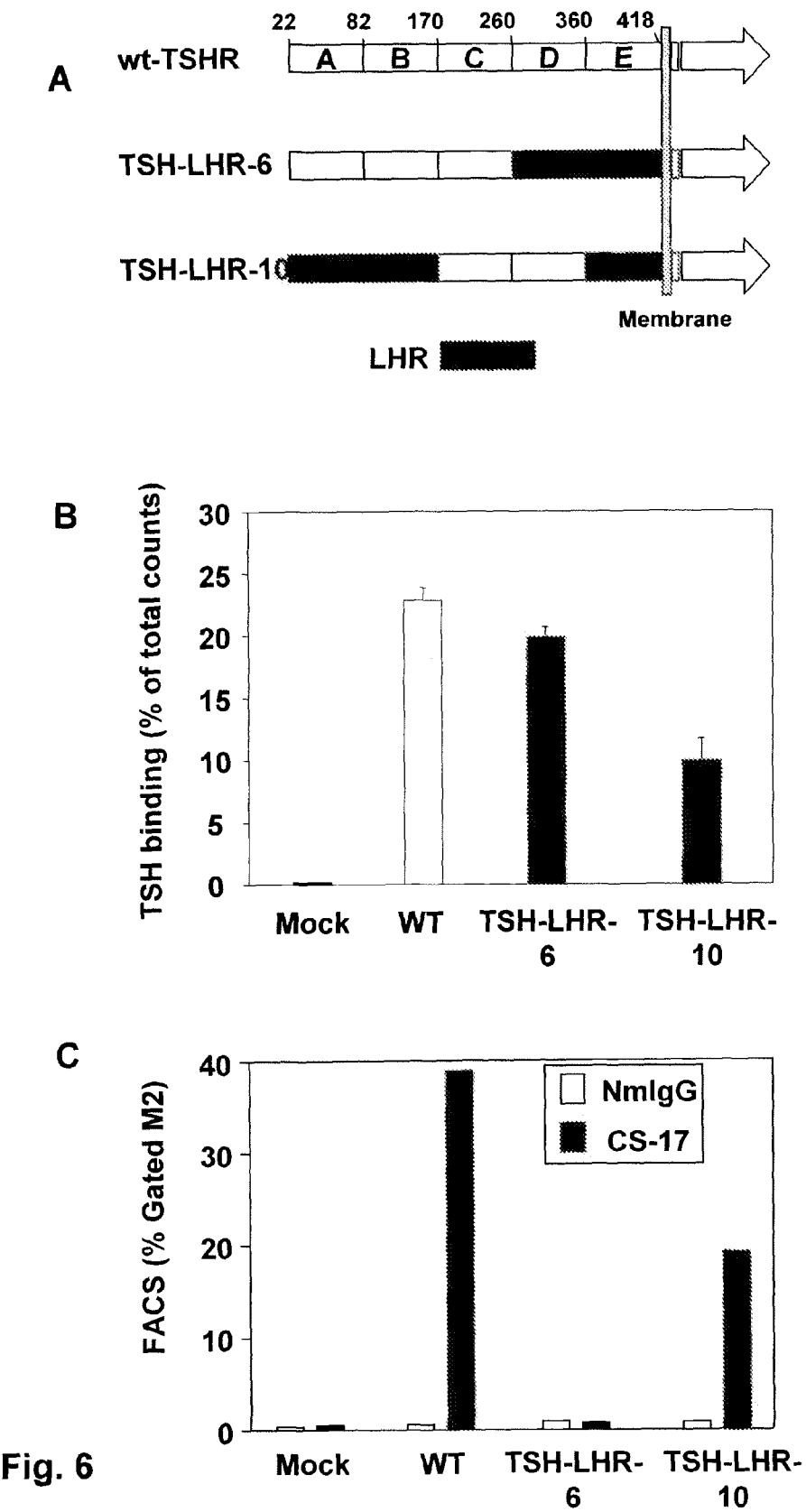
FIG. 6 depicts CS-17 recognition of chimeric TSH-LH receptors (TSH-LHR). COS-7 cells were transiently transfected with plasmids expressing the wild-type (wt) TSHR or the indicated TSH-LHR chimeras in accordance with an embodiment of the present invention. 'Mock' represents cells transfected with vector alone. Panel A: Schematic representation of selected chimeric TSH-LHR. For these receptors, the TSHR ectodomain was divided into 5 arbitrary domains (A-E) (Nagayama et al. 1991. Thyrotropin-luteinizing hormone/chorionic gonadotropin receptor extracellular domain chimeras as probes for TSH receptor function. *Proc. Natl. Acad. Sci. U.S.A.* 88:902-905.). Segments of the rat LHR (black bars) were substituted with the homologous regions of the wild-type (wt)TSHR (white bars). Panel B: Both TSH-LHR-6 and TSH-LHR-10 are expressed on the cell surface and bind $^{125}$I-TSH. TSH binding was assessed using cells in monolayer culture and was expressed (net of mock transfection values) as percent of total $^{125}$I-TSH added to the dishes (~10,000 cpm). Bars indicate the mean±SE of values obtained with triplicate dishes of cells. Panel C: CS-17 recognition of chimeric receptors on flow cytometry. Purified, normal mouse IgG (NmIgG) was used as a control (both preparations at 10 µg/ml). Of these chimeric receptors, CS-17 recognized only TSH-LHR-10.

The inventors also used flow cytometry to determine CS-17 recognition of selected chimeric receptors involving the substitution of TSHR segments with the luteinizing hormone receptor (LHR) (FIG. 6A) (Nagayama et al. 1991. Thyrotropin-luteinizing hormone/chorionic gonadotropin receptor extracellular domain chimeras as probes for TSH receptor function. *Proc. Natl. Acad. Sci. U.S.A.* 88:902-905.). In TSH-LHR-6, the C-terminal portion of the TSHR ectodomain (domains D and E) is substituted with the LHR. In TSH-LHR-10, only the middle portion of the TSHR ectodomain (residues 170-360; domains C and D) remain unchanged. As reported previously (Nagayama et al. 1991. Thyrotropin-luteinizing hormone/chorionic gonadotropin receptor extracellular domain chimeras as probes for TSH receptor function. *Proc. Natl. Acad. Sci. U.S.A.* 88:902-905.), both chimeras are expressed on the cell surface and bind TSH (FIG. 6B). On flow cytometry using aliquots of the same cells, CS-17 recognized the wild-type TSHR and TSH-LHR-10, but not TSH-LHR-6 (FIG. 6C). Taken together, these data suggest that a major (i.e., substantial) portion of the conformational (possibly discontinuous) CS-17 epitope lies between amino acid residues 170-260.

Example 13

CS-17 is, therefore, a rare example of a large molecule (IgG) that is a GPCR inverse agonist and representing a novel class of these agents that do not insert directly into a transmembrane helix pocket or bind to the extracellular loops. Having been generated by immunization with the TSHR A subunit, the mAb CS-17 epitopes lies within the ectodomain, upstream of amino acid residue 260. It is noteworthy that the TSHR ectodomain is, itself, a tethered inverse agonist (Vlaeminck-Guillem et al. 2002. Activation of the cAMP pathway by the TSH receptor involves switching of the ectodomain from a tethered inverse agonist to an agonist. *Mol. Endocrinol.* 16:736-746.). While not wishing to be bound by any particular theory, the inventors believe that mAb CS-17 enhances this suppressive activity and that further understanding of its mechanism of action will provide insight into this property of the TSHR ectodomain. Clearly, suppressing activity of a TSHR with very high constitutive activity consequent to an intracellular mutation (A623I) indicates that CS-17 is acting allosterically.

Example 14

In this light, CS-17 has a number of potential clinical applications. Perhaps the most common would be in reducing the risk of recurrence or progression of differentiated thyroid carcinoma following surgery and radio-iodine ablation of residual thyroid tissue. Because TSH stimulates thyrocyte growth (Vassart and Dumont. 1992. The thyrotropin receptor and the regulation of thyrocyte function and growth. *Endocr. Rev.* 13:596-611.), it is common practice after thyroid ablation to administer l-thyroxine at a supra-physiological dose to partially or completely suppress pituitary secretion of TSH (Biondi et al. 2005. Thyroid-hormone therapy and thyroid cancer: a reassessment. *Nat. Clin. Pract. Endocrinol. Metab* 1:32-40.). However, sustained mild elevations of peripheral thyroid hormone levels (subclinical thyrotoxicosis) carry the risk of cardiac arrhythmias and osteoporosis. More important, from the perspective of therapy for metastases of well-differentiated thyroid carcinomas, even total TSH suppression cannot eliminate the substantial TSH-independent constitutive activity of the TSHR in these metastases. Moreover, in such patients, serum T4 levels are determined by the dose of exogenously administered l-thyroxine, not on endogenous thyroid hormone production.

Therefore, suppression of TSHR constitutive activity with an inverse agonist such as CS-17 could be achieved while maintaining TSH and thyroid hormone levels within thephysiological range, reducing the risks mentioned above. Even at physiological TSH levels, the CS-17 effect on TSHR constitutive activity predominates over TSH responsiveness (FIG. 4C).

Example 15

Other potential situations for TSHR inverse agonist therapy would include a cooling off period in toxic nodular goiter prior to definitive surgical or radio-iodine therapy, particularly in elderly patients. The finding that CS-17 can reduce greatly elevated constitutive activity associated with TSHR mutations suggests that a TSHR inverse agonist could also be considered in rare instances of familial, non-autoimmune hyperthyroidism.

Finally, because CS-17 appears to act allosterically, it may be of value in treating amiodarone-induced, non-autoimmune thyrotoxicosis, a frequently serious condition in elderly patients with underlying cardiac conditions in whom thionamide drugs or radio-iodine therapy are not options for near-term relief (Bogazzi et al. 2001. The various effects of amiodarone on thyroid function. *Thyroid* 11:511-519).

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A purified antibody that binds specifically to a thyrotropin receptor ("TSHR') and has inverse agonist activity on the TSHR.

2. The purified antibody of claim 1, wherein the purified antibody is a monoclonal antibody produced by hybridoma CS-17, ATCC accession number PTA-8174.

3. The purified antibody of claim 1, having the same epitope specificity as a monoclonal antibody produced by hybridoma CS-17, ATCC accession number PTA-8174.

4. The purified antibody of claim 1, wherein the TSHR is a mutant TSHR comprising a mutation at C24, C29, C31, C41, S281, I486, I568, A623, or V656, or a combination thereof.

5. The purified antibody of claim 1 that binds specifically to the A-subunit of the TSHR.

6. The purified antibody of claim 1, wherein the TSHR is a polypeptide as disclosed by SEQ ID NO: 1.

7. The purified antibody of claim 1 that binds specifically to a conformational epitope of TSHR, wherein at least a substantial portion of the conformational epitope is located between amino acid residues 171 and 260 of the TSHR.

8. The purified antibody of claim 7, wherein the amino acid residues 171 through 260 are as disclosed by SEQ ID NO: 2.

9. The purified antibody of claim 1, wherein the TSHR is human TSHR.

10. The purified antibody of claim 1 that is humanized or a human antibody.

11. A purified antibody that binds specifically to a polypeptide that is encoded by a polynucleotide as disclosed by SEQ ID NO: 3 and has inverse agonist activity on the polypeptide.

12. The purified antibody of claim 11 that binds specifically to a conformational epitope on the polypeptide.

13. The purified antibody of claim 12, wherein a substantial portion of the conformational epitope is on a polypeptide that is encoded by a polynucleotide as disclosed by SEQ ID NO: 4.

14. The purified antibody of claim 11 that is humanized or is a human antibody.

15. A cell of hybridoma CS-17, ATCC accession number PTA-8174.

16. A kit for the treatment of a thyroid or thyroid or thyroid-related disease or disease condition in a subject in need thereof, comprising:
a purified antibody that binds specifically to thyrotropin receptor ("TSHR") and has inverse agonist activity on TSHR; and
instructions for using the purified antibody to treat the thyroid or thyroid-related disease or disease condition.

17. The kit of claim 16, wherein the purified antibody is a monoclonal antibody produced by hybridoma CS-17, ATCC accession number PTA-8174.

18. The purified antibody of claim 1, wherein the purified antibody is a Fab, Fab' or F(ab')2 fragment.

19. The purified antibody of claim 11, wherein the purified antibody is a Fab, Fab' or F(ab')2 fragment.

20. The kit of claim 16, wherein the purified antibody is a Fab, Fab' or F(ab')2 fragment.

21. The purified antibody of claim 1 that binds specifically to a conformational epitope of TSHR, wherein at least a substantial portion of the conformational epitope is located between amino acid residues 170 and 289 of the TSHR.

22. The purified antibody of claim 12, wherein at least a substantial portion of the conformational epitope is on a polypeptide that is encoded by nucleotides 508 through 867 of SEQ ID NO: 3.

23. The purified antibody of claim 4, wherein the mutation comprises (C29, 31S), (C24, 29S), (C24, 31S), S281I, I486F, I568T, A623I, or V656F, or a combination thereof.

* * * * *